(12) United States Patent
Hobbs

(10) Patent No.: US 8,258,097 B2
(45) Date of Patent: Sep. 4, 2012

(54) AMINO ACID DERIVATIVES

(75) Inventor: Christopher Hobbs, London (GB)

(73) Assignee: Proximagen Ltd., London (GB)

( * ) Notice: Subject to any disclaimer, the term of this patent is extended or adjusted under 35 U.S.C. 154(b) by 371 days.

(21) Appl. No.: 12/667,917

(22) PCT Filed: Jul. 4, 2008

(86) PCT No.: PCT/GB2008/002313
§ 371 (c)(1),
(2), (4) Date: Feb. 19, 2010

(87) PCT Pub. No.: WO2009/007696
PCT Pub. Date: Jan. 15, 2009

(65) Prior Publication Data
US 2010/0190725 A1   Jul. 29, 2010

(30) Foreign Application Priority Data

Jul. 6, 2007 (GB) .................... 0713189.9

(51) Int. Cl.
*A61K 38/05* (2006.01)
*A61K 31/198* (2006.01)
(52) U.S. Cl. .................... 514/17.7; 514/21.91
(58) Field of Classification Search .................... None
See application file for complete search history.

(56) References Cited

U.S. PATENT DOCUMENTS

| 3,859,331 A | 1/1975 | Kaiser et al. |
| 5,013,753 A | 5/1991 | Casagrande et al. |

FOREIGN PATENT DOCUMENTS

JP          54022337 A    2/1979

OTHER PUBLICATIONS

International Search Report for PCT/GB2008/002313 (WO 2009/007696 A1), issued on Oct. 3, 2008.

*Primary Examiner* — Christina Bradley
(74) *Attorney, Agent, or Firm* — Banner & Witcoff, Ltd.

(57) ABSTRACT

Compounds of formula (I) or formula (II) have dopaminergic activity: wherein: $R_1$ is a carboxyl, carboxyl ester, or carboxamide group; $R_2$ is a group —C(=O)—$NR_3R_4$, or —S(=O)$_2$—$NR_3R_4$; $R_3$ and $R_4$ are independently selected from hydrogen, optionally substituted $C_1$-$C_6$ alkyl, ($C_1$-$C_5$ fluoroalkyl)-$CH_2$—, -Q, and —$CH_2$Q, wherein Q is an optionally substituted monocyclic carbocyclic or heterocyclic ring of (3) to (6) ring atoms; or $R_3$ and $R_4$ together with the nitrogen to which they are attached form an optionally substituted monocyclic cycloalkyl or non-aromatic heterocyclic ring of (3) to (8) ring atoms; $R_5$ is hydrogen, or a natural or non-natural alpha amino acid residue linked via a peptide bond; $R_6$ is hydrogen or a group $R_7C$(=O)—; and $R_7$ is $C_1$-$C_6$ alkyl, $C_1$-$C_6$ fluoroalkyl or cyclopropyl.

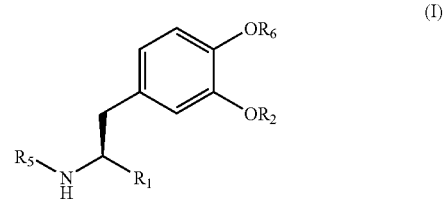

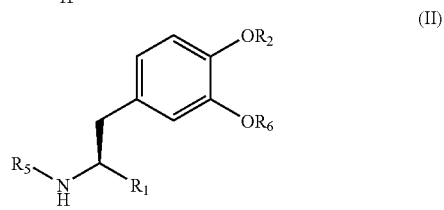

31 Claims, No Drawings

AMINO ACID DERIVATIVES

CROSS REFERENCE TO RELATED APPLICATIONS

This application is a National Stage application of co-pending PCT application PCT/GB2008/002313 filed Jul. 4, 2008, which claims the benefit of Great Britain application number 0713189.9 filed Jul. 6, 2007. These applications are incorporated herein by reference in their entireties.

The present invention relates to compounds which are substituted phenylalanine derivatives, and which diminish the symptoms of dopamine deficiency.

Dopamine is a substance produced naturally by neurons in the basal ganglia of the brain that allows smooth, co-ordinated control of voluntary movement. Loss of, or impairment of, dopamine-producing neurons in the brain is implicated in Parkinson's disease and related parkinson-plus syndromes. These conditions respond to dopamine replacement therapy. Other conditions, for example, Restless Legs Syndrome (RLS) also respond to dopamine replacement therapy.

Parkinson's disease is a progressive neurodegenerative disorder that affects neuronal cells in the substantia nigra in the mid-brain. It is an age-related disorder of the central nervous system primarily attacking people over the age of 60. Approximately one out of every 500 people contract the illness and approximately one out of every 100 people over the age of 60 develop the illness. As indicated above, Parkinson's Disease is thought to be caused by a deficiency of dopamine. The common symptoms include tremor, stiffness (or rigidity) of muscles, slowness of movement (bradykinesia) and loss of balance (postural dysfunction). Parkinson's Disease is one of the most prevalent neurodegenerative illnesses. The natural history of the disease is progressive and from 10-15 years from onset of the disease becomes disabling in most patients.

Parkinson's disease is largely sporadic and referred to as idiopathic in nature. Forms of the illness due to vascular incidents and to toxin exposure also exist. Rare familial forms of the illness also exist.

Many treatments have been tried since James Parkinson first described the condition in 1817. Current therapy for Parkinson's disease is based on dopamine replacement therapy based on the use of the dopamine precursor levodopa (or L-dopa) or dopaminergic compounds. L-dopa is highly effective in reversing the motor symptoms of the illness but on chronic treatment and with disease progression, its effectiveness declines. The duration of drug response is reduced and unpredictable fluctuations in movement occur. Treatment is associated with therapy limiting side effects which include involuntary movements (dyskinesia) and psychosis.

RLS is a neurosensorimotor disorder with parestethesias, sleep disturbances and, in most cases, periodic limb movements of sleep (PLMS). Two forms of RLS appear to exist: the idiopathic and the uremic form. RLS is characterised by (1) a desire to move the legs, usually associated with paresthesias/dysesthesias, (2) motor restlessness, (3) worsening or exclusive presence of symptoms at rest (i.e. lying, sitting) with at least partial or temporary relief by activity, and (4) worsening of symptoms during the evening or night.

The present invention provides compounds which are active as dopaminergic compounds or as compounds which diminish the symptoms of dopamine deficiency.

According to the invention, there is provided a compound which is a substituted phenylalanine of formula (I) or formula (II), or a salt, hydrate or solvate thereof:

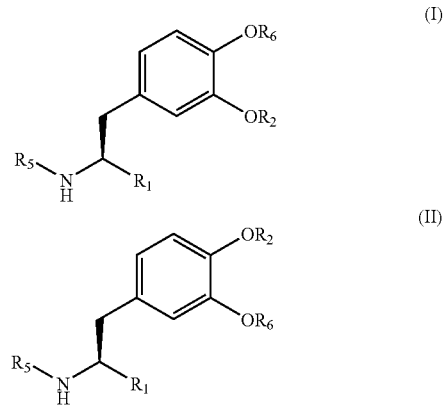

wherein:
$R_1$ is a carboxyl, carboxyl ester, or carboxamide group;
$R_2$ is a group —C(=O)—NR$_3$R$_4$, or —S(=O)$_2$—NR$_3$R$_4$;
$R_3$ and $R_4$ are independently selected from hydrogen, optionally substituted $C_1$-$C_6$ alkyl, ($C_1$-$C_5$ fluoroalkyl)-CH$_2$—, -Q, and —CH$_2$Q, wherein Q is an optionally substituted monocyclic carbocyclic or heterocyclic ring of 3 to 6 ring atoms; or $R_3$ and $R_4$ together with the nitrogen to which they are attached form an optionally substituted monocyclic cycloalkyl or non-aromatic heterocyclic ring of 3 to 8 ring atoms;
$R_5$ is hydrogen, or a natural or non-natural alpha amino acid residue linked via a peptide bond;
$R_6$ is hydrogen or a group $R_7$C(=O)—; and
$R_7$ is $C_1$-$C_6$ alkyl, $C_1$-$C_6$ fluoroalkyl or cyclopropyl.

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein, the term "($C_a$-$C_b$) fluoroalkyl" wherein a and b are integers refers to a ($C_a$-$C_b$)alkyl in which one or more hydrogen atoms are replced by fluorine. Thus when a is 1 and b is 3, for example, the term includes trifluotomethyl, difluoromethyl and monofluoromethyl.

As used herein the term "($C_a$-$C_b$)alkenyl" means a straight or branched chain alkenyl moiety having from a to b carbon atoms having at least one double bond of either E or Z stereochemistry where applicable. Thus when a is 2 and b is 6, the term includes, for example, vinyl, allyl, 1- and 2-butenyl and 2-methyl-2-propenyl.

As used herein the term "$C_2$-$C_6$ alkynyl" refers to straight chain or branched chain hydrocarbon groups having from a to b carbon atoms and having in addition one triple bond. Thus when a is 2 and b is 6, the term includes, for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the unqualified term "carbocyclic" refers to a mono-, bi- or tricyclic radical having up to 16 ring atoms, all of which are carbon, and includes aryl and cycloalkyl.

As used herein the unqualified term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, $(C_1-C_6)$ alkyl, $(C_2-C_6)$alkenyl, $(C_2-C_6)$alkynyl, $(C_1-C_6)$alkoxy, hydroxy, hydroxy$(C_1-C_6)$alkyl, $(C_1-C_3)$alkoxy$(C_1-C_3)$alkyl, mercapto, mercapto$(C_1-C_6)$alkyl, $(C_1-C_6)$alkylthio, halo (including fluoro, bromo and chloro), fully or partially fluorinated $(C_1-C_3)$alkyl, $(C_1-C_3)$alkoxy or $(C_1-C_3)$alkylthio such as trifluoromethyl, trifluoromethoxy, and trifluoromethylthio, nitro, nitrile (—CN), oxo (=O), phenyl, phenyl$(C_1-C_3)$alkyl-, phenoxy, monocyclic heteroaryl, heteroaryl$(C_1-C_3)$alkyl-, or heteroaryloxy with 5 or 6 ring atoms, cycloalkyl having 3 to 6 ring carbon atoms, —COOR$^A$, —COR$^A$, —OCOR$^A$, —SO$_2$R$^A$, —CONR$^A$R$^B$, —CONHNH$_2$, —SO$_2$NR$^A$R$^B$, —NR$^A$R$^B$, —NHNH$_2$, —OCONR$^A$R$^B$, —NR$^B$COR$^A$, —NR$^B$COOR$^A$, —NR$^B$SO$_2$OR$^A$ or —NR$^A$-CONR$^A$R$^B$ wherein R$^A$ and R$^B$ are independently hydrogen or a $(C_1-C_6)$alkyl, hydroxy$(C_1-C_6)$alkyl, or $(C_1-C_3)$alkoxy$(C_1-C_3)$alkyl group or, in the case where R$^A$ and R$^B$ are linked to the same N atom, R$^A$ and R$^B$ taken together with that nitrogen may form a cyclic amino ring such as morpholinyl, piperidinyl, piperazinyl, or 4-$(C_1-C_6)$alkyl-piperizinyl such as 4-methyl-piperazinyl. Where the substituent is phenyl, phenyl$(C_1-C_3)$alkyl-, phenoxy or monocyclic heteroaryl, heteroaryl$(C_1-C_3)$alkyl-, or heteroaryloxy with 5 or 6 ring atoms, the phenyl or heteroaryl ring thereof may itself be substituted by any of the above substituents except phenyl, phenyl$(C_1-C_3)$alkyl-, phenoxy, heteroaryl, heteroaryl$(C_1-C_3)$alkyl-, or heteroaryloxy. An "optional substituent" or "substituent" may be one of the foregoing specified groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like. For a review on suitable salts, see *Handbook of Pharmaceutical Salts: Properties, Selection, and Use* by Stahl and Wermuth (Wiley-VCH, Weinheim, Germany, 2002).

In the compounds of the invention, carbon atom to which $R_1$ is attached is assymmetric, and the stereochemistry at that centre is as shown in formula (I). However, the compounds of the invention may contain one or more additional chiral centres, because of the presence of asymmetric carbon atoms, and they can exist as a number of diastereoisomers with R or S stereochemistry at each chiral centre. The invention includes all such diastereoisomers and mixtures thereof.

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

The Group $R_1$ $R_1$ may be a carboxyl group (—COOH), a carboxyl ester group or a carboxamide group. Compounds wherein $R_1$ is a carboxyl ester group form one presently preferred subclass.

Examples of carboxyl ester groups $R_1$ include those of formula —COOR$^C$ wherein R$^C$ is a $C_1-C_6$ alkyl such as methyl, ethyl, and n- or iso-propyl, or a $C_2-C_6$ alkenyl group such as allyl. A presently preferred carboxyl ester group is the methyl ester —COOCH$_3$.

Examples of carboxamide groups $R_1$ include those of formula CONR$^B$(Alk)$_n$R$^A$ wherein Alk is an optionally substituted divalent $C_1-C_6$ alkylene, or $C_2-C_6$ alkenylene or $C_2-C_6$ alkynylene radical such as —CH$_2$—, —CH$_2$CH$_2$—, —CH$_2$CH$_2$CH$_2$—, —CH$_2$CH=CH—, and —C≡C—;

n is 0 or 1,

R$^B$ is hydrogen or a $C_1-C_6$ alkyl such as methyl or ethyl or $C_2-C_6$ alkenyl group such as allyl, R$^A$ is hydrogen, hydroxy or optionally substituted carbocyclic or heterocyclyl, or R$^A$ and R$^B$ taken together with the nitrogen to which they are attached form an N-heterocyclic ring which may optionally contain one or more additional hetero atoms selected from O, S and N, and which may optionally be substituted on one or more ring C or N atoms.

Thus, in carboxamide groups $R_1$ of formula —CONR$^B$(Alk)$_n$R$^A$, Alk may be optionally substituted —CH$_2$—, —CH$_2$CH$_2$—, —CH$_2$CH$_2$CH$_2$—, —CH$_2$CH=CH—, or —CH$_2$C≡CCH$_2$—; R$^B$ may be hydrogen or methyl, trifluoromethyl, ethyl, n- or iso-propyl, or allyl; R$^A$ may be hydroxy or optionally substituted phenyl, 3,4-methylenedioxyphenyl, pyridyl, furyl, thienyl, N-piperazinyl, or N-morpholinyl; or R$^A$ and R$^B$ taken together with the nitrogen to which they are attached form an N-heterocyclic ring which may optionally contain one or more additional hetero atoms selected from O, S and N, and which may optionally be substituted on one or more ring C or N atoms.

A presently preferred carboxamide group $R_1$ is —$CONH_2$.

The Group $R_2$ $R_2$ is a carbamate group —C(=O)—$NR_3R_4$, or a sulfamate group —S(=O)$_2$—$NR_3R_4$, wherein $R_3$ and $R_4$ are independently selected from
hydrogen,
optionally substituted $C_1$-$C_6$ alkyl, for example methyl, ethyl, or n- or iso-propyl,
($C_1$-$C_5$ fluoroalkyl)-$CH_2$—, such as —$CH_2CF_3$;
-Q, and —$CH_2Q$, wherein Q is an optionally substituted monocyclic carbocyclic ring of 3 to 6 ring atoms, for example cyclopropyl, cyclopentyl, cyclohexyl or phenyl, or an optionally substituted heterocyclic ring of 3 to 6 ring atoms, for example furyl, thienyl, pyridyl, pyrimidinyl, pyrrolyl, pyrazinyl, oxazolyl, thiazolyl, azetidinyl, pyrrolidinyl, piperidinyl, piperazinyl, or morpholinyl or $R_3$ and $R_4$ together with the nitrogen to which they are attached form an optionally substituted monocyclic cycloalkyl or non-aromatic heterocyclic ring of 3 to 8 ring atoms, for example pyrrolidinyl, piperidinyl, piperazinyl, or morpholinyl.

Presently it is preferred that $R_2$ should be a carbamate group.

In one sub-class of compounds of the invention, one of $R_3$ and $R_4$ is hydrogen, and the other is optionally substituted $C_1$-$C_3$ alkyl, especially methyl.

In another sub-class of compounds of the invention, $R_3$ and $R_4$ together with the nitrogen to which they are attached form an optionally substituted piperidinyl, piperazinyl, morpholinyl or pyrrolidinyl ring.

Any optional substituents referred to above in connection with $R_3$ and $R_4$ may be selected from trifluoromethyl, $C_1$-$C_4$ alkoxy such as methoxy, trifluoromethoxy, halogen, cyano, hydroxy, mercapto, oxo, —$NH_2$, —$NHR^A$, or —$NR^AR^B$ wherein $R^A$ and $R^B$ are independently methyl or ethyl.

The Group $R_5$ $R_5$ is hydrogen or a natural or non-natural alpha amino acid residue linked via a peptide bond.

Thus, in one distinct sub-class of compounds of the invention $R_5$ is hydrogen.

When the group $R_5$ is not hydrogen, the compounds of the invention include those wherein $R_5$ is an alpha amino acid residue of formula —C(=O)C($R_8$)($R_9$)$NH_2$, wherein $R_8$ and $R_9$ are independently
(a) hydrogen; or
(b) the side chain of a natural amino acid, or
(c) optionally substituted $C_1$-$C_4$ alkyl, $C_1$-$C_4$ alkoxy, $C_2$-$C_4$ alkenyl, $C_2$-$C_4$ alkenyloxy, or $C_2$-$C_4$ alkynyl, or
(d) —$CH_2XCH_3$, —$CH_2CH_2XCH_3$, or —$CH_2XCH_2CH_3$, wherein X is —O—, S, or —$NR_{10}$ wherein $R_{10}$ is hydrogen, methyl or ethyl; or
(e) —$CH_2Q$ or $CH_2OQ$ wherein Q is as defined in relation to formula (I) or (II) above; or $R_8$ and $R_9$ taken together with the carbon atom to which they are attached form an optionally substituted cycloalkyl or heterocyclic ring of 3 to 8 ring atoms, optionally fused to a second, optionally substituted, carbocyclic or heterocyclic ring.

In compounds of the type wherein $R_5$ is an alpha amino acid residue of formula —C(=O)C($R_8$)($R_9$)$NH_2$, $R_8$ and $R_9$ are independently optionally substituted $C_1$-$C_4$ alkyl, phenyl, benzyl cyclopropyl, cyclobutyl, cyclopentyl, cyclohexyl, cyclopropylmethyl, cyclobutylmethyl, cyclopentylmethyl, cyclohexylmethyl, pyridyl, pyridylmethyl, piperidinyl, piperazinyl or morpholinyl.

In one distinct sub-class of compounds wherein $R_5$ is an alpha amino acid residue of formula —C(=O)C($R_8$)($R_9$)$NH_2$, one of $R_8$ and $R_9$ is hydrogen. For example $R_8$ may be hydrogen and $R_9$ may be —$CH_2Q$ wherein Q is optionally substituted phenyl, wherein optional substituents include hydroxy.

In another distinct sub-class of compounds wherein $R_5$ is an alpha amino acid residue of formula —C(=O)C($R_8$)($R_9$)$NH_2$, one of $R_8$ and $R_9$ is hydrogen and the other is the side chain of a natural amino acid.

Specifically, in compounds wherein $R_5$ is an alpha amino acid residue of formula —C(=O)C($R_8$)($R_9$)$NH_2$, $R_8$ and $R_9$ may each be methyl, or one of $R_6$ and $R_7$ may be hydrogen and the other methyl.

In yet another distinct sub-class of compounds wherein $R_5$ is an alpha amino acid residue of formula —C(=O)C($R_8$)($R_9$)$NH_2$, $R8_6$ and $R_9$ taken together with the carbon atom to which they are attached may form a $C_1$-$C_6$ cycloalkyl ring, which is optionally benz-fused. For example, $R_8$ and $R_9$ taken together with the carbon atom to which they are attached may form a cyclopropyl, cyclobutyl, cyclopentyl or cyclohexyl ring.

In compounds of the type wherein $R_5$ is an alpha amino acid residue of formula —C(=O)C($R_8$)($R_9$)$NH_2$, any optional substituents in $R_8$ and $R_9$ may be selected from, for example, methyl, trifluoromethyl, methoxy, trifluoromethoxy, cyclopropyl, halogen, cyano, hydroxy, mercapto, oxo, —$NH_2$, —$NHR^A$, or —$NR^AR^B$ wherein $R^A$ and $R^B$ are independently methyl or ethyl.

Presently preferred compounds of the invention include those of formula (I) or (II) as defined and discussed above, wherein $R_5$ is a group of formula (III):

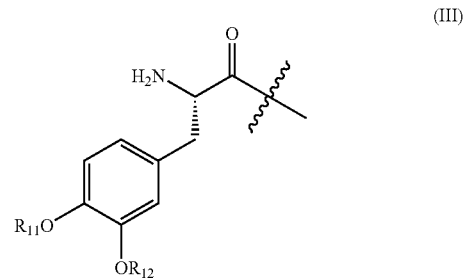

(III)

wherein (a) $R_{11}$ and $R_{12}$ are independently selected from hydrogen, groups $R_6$ as defined in relation to formula (I) or (II) and as discussed above, groups —C(=O)$OR_{13}$ or groups —C(=O)$OR_{13}$ wherein $R_{13}$ is $C_1$-$C_3$ alkyl; or (b) one of $R_{11}$ and $R_{12}$ is hydrogen and the other is a group $R_2$ as defined in relation to formula (I) or (II) and as discussed above. In formula (III), $R_{11}$ and $R_{12}$ may each hydrogen.

A presently preferred class of compounds of the invention has formula (IV) or formula (V), and salts, hydrates and solvates thereof:

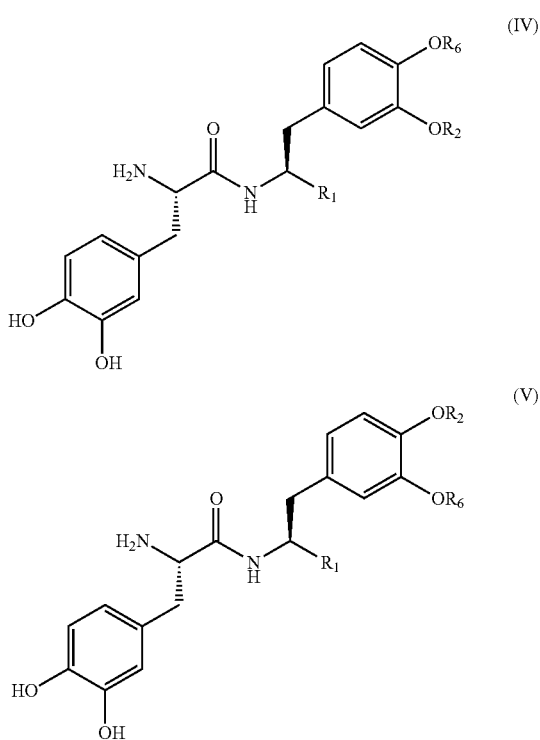

wherein $R_1$ is a group $R_{14}O(C=O)—$; $R_2$ is a group $R_{15}NH(C=O)—$; and $R_6$ is hydrogen or a group $R_{16}(C=O)—$, wherein $R_{14}$, $R_{15}$, and $R_{16}$ are independently selected from $C_1$-$C_6$ alkyl, $C_1$-$C_6$ fluoroalkyl and cyclopropyl.

In such compounds (IV) and (V), $R_{14}$, $R_{15}$, and $R_{16}$ are each preferably selected from methyl or trifluoromethyl.

Examples of specific compound structures of the invention include those of the examples herein.

Synthetic Routes

There are multiple synthetic strategies for the synthesis of the compounds (I) with which the present invention is concerned, but all rely on chemistry known to the synthetic organic chemist. Compounds according to formula (I) can be synthesised according to procedures described in the standard literature and are well-known to the one skilled in the art. Typical literature sources are "*Advanced organic chemistry*", 4<sup>th</sup> Edition (Wiley), J March, "*Comprehensive Organic Transformation*", 2<sup>nd</sup> Edition (Wiley), R. C. Larock, "*Handbook of Heterocyclic Chemistry*", 2<sup>nd</sup> Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*SciFinder*" or "*Beilstein*".

Often in the synthesis of the compounds of the invention, it is expedient to protect selected reactive groups to force reaction at a particular reactive centre. Methods for the protection of reactive groups are generally described in McOmie, Protective Groups in Organic Chemistry, Plenum Press, N.Y., 1973 and Greene and Wutz, Protecting Groups in Organic Synthesis, 2d, ed., John Wiley & Sons, N.Y., 1991.

In general the compounds of the invention are accessible by methods analogous to those of the Examples herein. Thus compounds (IA)

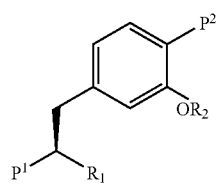

wherein $P^1$ is a protected amino group such as a tert-butoxycarbonylamino group, $P^2$ is a protected hydroxyl group such as a benzyloxy group and $R_1$ is an ester group, may be prepared by condensing the desired $R_2$ group onto the 3-hydroxy group of the phenyl ring of precursor (IB)

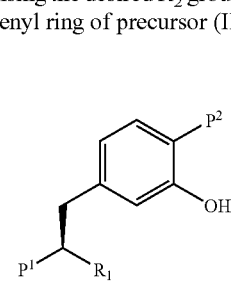

For example, isocyanates, carbamoyl chlorides and sulphamoyl chlorides are suitable reagents for such condensation.

Likewise compounds of formula (IIA)

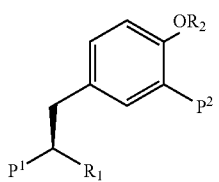

wherein $P^1$ is a protected amino group such as a tert-butoxycarbonylamino group, $P^2$ is a protected hydroxyl group such as a benzyloxy group and $R_1$ is an ester group, may be prepared by condensing the desired $R_2$ group onto the 3-hydroxy group of the phenyl ring of precursor (IIB)

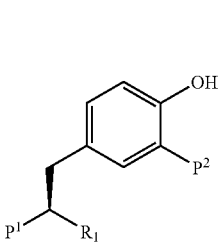

For example, suitable reagents for such condensation are activated carbamates and sulphamates. Thus N-succinimidyl N-methylcarbamate introduces the $R_2$ group —$CONHCH_3$.

Compounds (IA) and (IIA) may then be modified by removal of the protecting group from $P_1$, and the resultant free amino group may then be modified to introduce the desired $R_5$ substituent, before removal of the protecting group from $P_2$.

Compounds (IA) and (IIA) may also be modified by hydrolysis of the ester group $R_1$ to form a carboxyl group, which then may optionally be amidated to from a carboxamide group, The protecting group may then be removed from $P_1$, and the resultant free amino group optionally modified to introduce the desired $R_5$ substituent, before removal of the protecting group from $P_2$.

Compounds (I) and (II) wherein $R_5$ is a natural or non-natural alpha amino acid residue linked via a peptide bond may be prepared by standard methods of peptide synthesis from the corresponding appropriately protected compounds (IA) and (IB) wherein $R_5$ is hydrogen. Methods of peptide synthesis are of course extremely well known, see for example "The practice of peptide synthesis", 2nd ed., by M. Bodansky and A. Bodansky, Springer-Verlag, New York. XVIII.

Pharmaceutical Utility

As mentioned, compounds of the invention are active as dopaminergic compounds or as compounds which diminish the symptoms of dopamine deficiency. Some or all of such activity may be due to the in vivo conversion of the compound to L-dopa, ie such compounds act as full or partial prodrugs of L-dopa. Conversion in vivo of compounds of the invention can result in more prolonged systemic exposure and/or higher peak concentration exposure to L-dopa than by administration of L-dopa itself, especially when the $R_5$ group of the compounds of the invention has formula (III) above.

Compounds of the present invention are useful in a method of treatment of a condition associated with impaired dopaminergic signalling in a subject, comprising administering to the subject an amount of the compound effective to reduce such impairment. The compounds are also useful in the preparation of a composition for treatment of a condition associated with impaired dopaminergic signalling. Examples of such conditions include Parkinson's disease, or Restless Legs Syndrome, as well as Tourette's syndrome, attention deficit hyperactive disorder, generation of pituitary tumours, a parkinson-plus syndrome, levodopa responsive dystonia, dyskinesia, periodic movements in sleep, dysphagia or neuroleptic malignant syndrome.

Typical examples of Parkinson's disease which can be treated with compounds of the invention include sporadic Parkinson's disease, familial forms of Parkinson's disease and post-encephalitic Parkinsonism.

Typical examples of Parkinson-plus syndromes which can be treated with compounds of the invention include progressive supranuclear palsy and multiple system atrophy.

Typically, the dyskinesia is L-dopa-induced dyskinesia.

Compounds of the invention may be administered in a variety of dosage forms. Thus, they can be administered orally, for example as tablets, capsules, troches, lozenges, aqueous or oily suspensions, dispersible powders or granules.

The compounds can be administered in a sublingual formulation, for example a buccal formulation. The compounds of the invention may also be administered parenterally, whether subcutaneously, intravenously, intramuscularly, intrasternally, transdermally, by inhalation, intranasally, or by infusion techniques. The compounds may also be administered as suppositories. Thus, the compounds of the invention are administered orally, or by inhalation, or intranasally, but preferably the compounds of the invention are administered orally and more preferably, the compounds of the invention are administered as a tablet or capsule. In the latter connection, administration of the compounds in a hard gelatine capsule form, or in one of the many sustained release formulations known in the art will often be preferred.

The present invention further provides a pharmaceutical composition containing a compound of the invention or a pharmaceutically acceptable salt thereof, as defined above, and a pharmaceutically acceptable carrier.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol. Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Since the compounds of the invention are preferably administered orally, the present invention further provides a pharmaceutical composition containing a compound of the invention or a pharmaceutically acceptable salt thereof, as defined above, and a pharmaceutically acceptable carrier in the form of a capsule or tablet.

Solutions for injection or infusion may contain as carrier, for example, sterile water or preferably they may be in the form of sterile, aqueous, isotonic saline solutions.

The compounds of the present invention may also be administered with other active compounds which have previously been shown to be beneficial in L-dopa therapy, and may also be administered together with L-dopa itself. For example, L-dopa has previously been co-administered with peripheral decarboxylase inhibitors and with catechol-O-methyltransferase (COMT) inhibitors. The present invention therefore provides a pharmaceutical composition containing a compound of the invention or a pharmaceutically acceptable salt thereof as defined above, a peripheral decarboxylase inhibitor and/or a COMT inhibitor, and a pharmaceutically acceptable carrier or diluent. A suitable decarboxylase inhibitor is carbidopa or benserazide. Preferably the peripheral decarboxylase inhibitor is carbidopa. A suitable COMT inhibitor is entacapone.

Also provided is a product comprising (a) a compound of the invention or a pharmaceutically acceptable salt thereof as defined above and (b) a peripheral decarboxylase inhibitor and/or (c) a COMT inhibitor, for simultaneous separate or sequential use in the treatment of the human or animal body.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the art. However, it is expected that a typical dose will be in the range from about 0.001 to 50 mg per kg of body weight.

The following examples illustrate the invention:

Abbreviations:

DMA N,N-Dimethylacetamide

DMAP 4-N,N-Dimethylaminopyridine

DMF N,N-Dimethylformamide

EDCI 3-Dimethylaminopropyl-N-ethylcarbodiimide hydrochloride

HBTU Benzotriazolyl N,N,N,N-tetramethyluronium hexafluorophosphate

HOBT N-Hydroxybenzotriazole

DMF N,N-Dimethylformamide

TFA Trifluoroacetic acid

HPLC/MS Method

Method A

HPLC/MS data was obtained using an HP1100 LC combined with a Waters Micromass ZMD mass spectrometer operating in positive ion mode. A Genesis 4 micron C18 column was used and samples were eluted with a gradient made up from two solvents: 0.1% aqueous formic acid and 0.1% formic acid/acetonitrile. The gradient rose from 5% acetonitrile to 95% over a period of 7 minutes and was held at 95% for 3 minutes before dropping to 5% over 4 minutes.

Method B

HPLC/MS data was obtained on a Thermo Finnegan Surveyor LC system interfaced directly with a Thermo Finnegan LCQ DECA XP ion trap mass spectrometer. An Alltech Prevail 3 micron C18 column was used and samples were eluted with a gradient made up from solvent A (10 mM ammonium acetate in 0.1% formic acid/water) solvent B (50 mL of solvent A in 0.1% formic acid/acetonitrile). The gradient rose from 5% solvent B to 95% over a period of 6 minutes and was held at 95% for 2 minutes before dropping to 5% over 0.5 minutes.

HPLC Method

HPLC data was obtained using Waters Alliance HPLC instrument (2695 separations module). A Kromasil 5 um (250 mm×4.6 mm) C18 column was used and samples were eluted with a gradient made up from three solvents: solvent A (water), solvent B (acetonitrile) and solvent C (2% TFA in water). The gradient used is summarised in the gradient table below.

| Time | Flow (mL/min) | % A | % B | % C |
| --- | --- | --- | --- | --- |
| 0 | 1 | 90 | 5 | 5 |
| 14 | 1 | 39.6 | 55.4 | 5 |
| 14.2 | 1 | 90 | 5 | 5 |
| 19 | 1 | 90 | 5 | 5 |
| 20 | 1 | 90 | 5 | 5 |

1H nmr Method 1H nmr data was obtained on a Bruker AMX400, a Bruker Avance 400 or a Jeol ECA 500 MHz machine.

MS Method

Mass spectrometry data was obtained using a ThermoFinnigan LCQ DECA XP directly interfaced with a ThermoFinnigan Surveyor LC system.

EXAMPLE 1

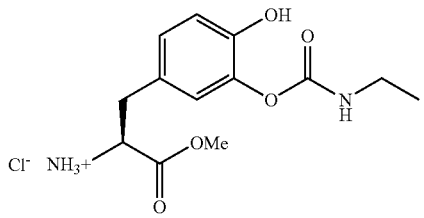

(S)-2-(3-Ethylcarbamoyloxy-4-hydroxy-phenyl)-1-methoxycarbonyl-ethyl-ammonium chloride Step 1

(S)-3-(3-Benzyloxy-4-hydroxy-phenyl)-2-tert-butoxycarbonylamino-propionic acid methyl ester and (S)-3-(4-benzyloxy-3-hydroxy-phenyl)-2-tert-butoxycarbonylamino-propionic acid methyl ester (S)-2-tert-Butoxycarbonylamino-3-(3,4-dihydroxy-phenyl)-propionic acid methyl ester (14.5 g) was dissolved in acetone (340 ml). Potassium carbonate (19.3 g) and sodium iodide (1.05 g) were added followed by benzyl chloride (5.58 ml; 1.04 eq). The reaction mixture was stirred at room temperature under nitrogen for 15 min and then heated to reflux for 10 hr. The precipitated solid was removed by filtration and the filtrate evaporated to dryness giving a brown oil. The crude product was purified by chromatography on silica gel eluting with a gradient of ethyl acetate-hexane (from 5% to 25% ethyl acetate).

The first eluted isomer was (S)-3-(3-benzyloxy-4-hydroxy-phenyl)-2-tert-butoxycarb-onylamino-propionic acid methyl ester, 1.62 g; Rf 0.16 (25% ethyl acetate-hexane); NMR (500 MHz, d6 DMSO) 1.42 (9H, s), 2.95-3.05 (2H, m), 3.67 (3H, s), 4.53-4.54 (1H, m), 4.95-4.97 (1H, m), 5.07 (2H, s), 5.56 (1H, s), 6.63 (1H, br d J 8), 6.71 (1H, br s), 6.85 (1H, d J8), 7.3-7.4 (5H, m); HPLC/MS Retention time 5.99 min, m/z 402 (MH+).

The second eluted isomer was (S)-3-(4-Benzyloxy-3-hydroxy-phenyl)-2-tert-butoxy-carbonylamino-propionic acid methyl ester, 4.15 g; Rf 0.14 (25% ethyl acetate-hexane); NMR (500 MHz, d6 DMSO) 1.42 (9H, s), 2.97-2.99 (2H, m), 3.72 (3H, s), 4.52-4.54 (1H, m), 4.96-4.97 (1H, m), 5.07 (2H, s), 5.61 (1H, s), 6.58 (1H, dd J 8, 2), 6.71 (1H, d J ca 2), 6.84 (1H, d J 8), 7.35-7.41 (5H, m); HPLC/MS retention time 6.05 min, m/z 402 (MH+).

Step 2

(S)-3-(4-Benzyloxy-3-ethylcarbamoyloxy-phenyl)-2-tert-butoxycarbonylamino-propionic acid methyl ester (S)-3-(4-Benzyloxy-3-hydroxy-phenyl)-2-tert-butoxycarbonylamino-propionic acid methyl ester (2.8 g) was dissolved in dichloromethane (60 ml) and a catalytic amount of DMAP was added. Ethyl isocyanate (0.8 ml) was added and the solution stirred and heated at 60 C for 4 hours. The reaction was monitored by HPLC/MS and further portions of ethyl isocyanate added and heating continued until the reaction was complete.

The reaction mixture was evaporated to dryness and the crude product recrystallised from ethyl acetate-hexane. (S)-3-(4-Benzyloxy-3-ethylcarbamoyloxy-phenyl)-2-tert-butoxycarbonylamino-propionic acid methyl ester was obtained as a white solid, 2.2 g; NMR (500 MHz, CDCl3) 1.15 (3H, t J 7.2), 1.42 (9H, s), 2.97-3.02 (2H, m), 3.28 (2H, dq J 7, 6.6), 3.70 (3H, s), 4.5-4.55 (2H, br), 4.95-5.0 (2H, br), 5.06 (2H, s), 6.88-6.92 (3H, m), 7.28-7.42 (5H, m); HPLC/MS retention time 6.19 min, m/z 473 (MH+).

Step 3

(S)-2-(3-Ethylcarbamoyloxy-4-hydroxy-phenyl)-1-methoxycarbonyl-ethyl-ammonium chloride (S)-3-(4-Benzyloxy-3-ethylcarbamoyloxy-phenyl)-2-tert-butoxycarbonylamino-propionic acid methyl ester (220 mg) was dissolved in 4M HCl in dioxane (3 ml) and the solution was left at room temperature for ca 2 hr. Evaporation of solvent gave a white solid which was redissolved in methanol (5 ml) and hydrogenated at 1 atmosphere of hydrogen gas over 5% palladium-carbon (44 mg). After stirring overnight at room temperature the catalyst was removed by filtration and washed with methanol. Evaporation of the filtrate gave a gum which was crystallised from methanol-ether. (S)-2-(3-Ethylcarbamoyloxy-4-hydroxy-phenyl)-1-methoxycarbonyl-ethyl-ammonium chloride was obtained as a white solid, 110 mg; NMR (500 MHz, d6 DMSO) 1.07 (3H, t J 7), 2.94-3.09 (4H, m), 3.67 (3H, s), 4.18 (1H, t J 6), 6.84 (3H, br s), 7.56 (1H, t J 5.5), 8.43 (ca 3H, br s), 9.55 (1H, s); HPLC/MS retention time 3.41 min, m/z 283 (MH+).

EXAMPLE 2

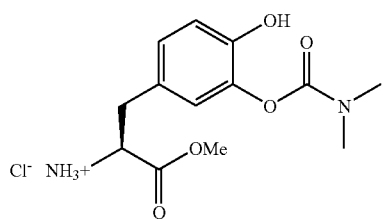

(S)-2-(3-Dimethylcarbamoyloxy-4-hydroxy-phenyl)-1-methoxycarbonyl-ethyl-ammonium chloride Step 1

(S)-3-(4-Benzyloxy-3-dimethylcarbamoyloxy-phenyl)-2-tert-butoxycarbonylamino-propionic acid methyl ester (S)-3-(4-Benzyloxy-3-hydroxy-phenyl)-2-tert-butoxycarbonylamino-propionic acid methyl ester (401 mg) was dissolved in dichloromethane (8 ml) and N,N-dimethylcarbamoyl chloride (0.092 ml, 1eq) added. Triethylamine (0.14 ml, 1 eq) was added and the mixture was stirred and heated under reflux. The reaction was monitored by HPLC/MS and further portions of N,N-dimethylcarbamoyl chloride and triethylamine were added in order to complete the reaction. After a total of 8 hours reflux the reaction mixture was evaporated to dryness and absorbed onto silica gel. Chromatography, eluting with mixtures of ethyl acetate-hexane afforded (S)-3-(4-Benzyloxy-3-dimethylcarbamoyloxy-phenyl)-2-tert-butoxycarbonylamino-propionic acid methyl ester as an oil, 315 mg; Rf 0.14 (ethyl acetate-hexane 1:3); HPLC/MS retention time 3.89 min, m/z 473 (MH+). Crystallisation from ethyl acetate-hexane gave (S)-3-(4-benzyloxy-3-dimethylcarbamoyloxy-phenyl)-2-tert-butoxycarbonyl-amino-propionic acid methyl ester as a white solid, 126 mg; NMR (500 MHz, CDCl3) 1.42 (9H, s), 2.95 (3H, s), 2.98-3.04 (5H, m), 3.70 (3H, s), 4.52-4.54 (ca 1H, m), 4.97-5.00 (ca 1H, br d), 5.05 (2H, s), 6.88-6.92 (3H, m), 7.28-7.40 (5H, m).

Step 2

(S)-2-(3-Dimethylcarbamoyloxy-4-hydroxy-phenyl)-1-methoxycarbonyl-ethyl-ammonium chloride (S)-3-(4-Benzyloxy-3-dimethylcarbamoyloxy-phenyl)-2-tertbutoxycarbonylamino-propionic acid methyl ester (122 mg) was dissolved in 4M HCl in dioxane (2 ml) and the solution was left at room temperature. After 1 hr evaporation of solvent gave a white solid which was redissolved in methanol (5 ml) and hydrogenated at 1 atmosphere of hydrogen gas over 5% palladium-carbon (20 mg). After stirring for 1 hr at room temperature the catalyst was removed by filtration and washed with methanol. Evaporation of the filtrate gave a gum which was crystallised by trituration with methanol-ether. (S)-2-(3-Dimethylcarbamoyloxy-4-hydroxy-phenyl)-1-methoxy-carbonyl-ethyl-ammonium chloride was obtained as a white solid, 77 mg; HPLC/MS Retention time 3.85 min, m/z 283 (MH+); NMR (500 MHz, d6 DMSO) 2.89 (3H, s), 2.95-3.02 (2H, m) overlaps 3.03 (3H, s), 3.67 (3H, s), 4.19 (1H, t J 7), 6.83-6.88 (3H, m), 8.40 (ca 3H, br exch D2O), 9.56 (1H, s, exch D2O).

EXAMPLE 3

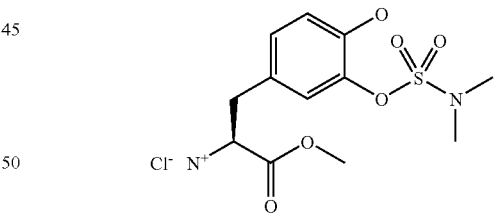

(S)-2-(3-Dimethylsulfamoyloxy-4-hydroxy-phenyl)-1-methoxycarbonyl-ethyl-ammonium chloride Step 1

(S)-2-Benzyloxycarbonylamino-3-(4-benzyloxy-3-dimethylsulfamoyloxy-phenyl)-propionic acid methyl ester (S)-2-Benzyloxycarbonylamino-3-(4-benzyloxy-3-hydroxy-phenyl)-propionic acid methyl ester (575 mg) (L. Hunter and C. Hutton, Aust. J. Chem., 2003, 56, 1095-1098) was dissolved in dichloromethane (12 ml) and N,N-dimethylsulfamoyl chloride (0.17 ml) added. Triethylamine (0.36 ml) was added dropwise followed by a catalytic amount of DMAP. The mixture was stirred and heated at 55° C. overnight. The reaction was monitored by HPLC/MS and further portions of N,N-dimethylsulphamoyl chloride (0.08 ml) and triethylamine (0.18 ml) were added and heating continued at 55 C for 24 hours.

The reaction mixture was diluted with dichloromethane and washed with dil HCl, with aq sodium bicarbonate and with brine. Drying (MgSO4) and evaporation gave the crude product. Silica gel chromatography, eluting with mixtures of ethyl acetate-hexane gave (S)-2-benzyloxycarbonylamino-3-(4-benzyloxy-3-dimethylsulfamoyloxy-phenyl)-propionic acid methyl ester as a colourless gum, 615 mg; Rf 0.37 (ethyl acetate-hexane 1:1); HPLC/MS retention time 7.03 min, m/z 507 (MH+).

Step 2

(S)-2-(3-Dimethylsulfamoyloxy-4-hydroxy-phenyl)-1-methoxycarbonyl-ethyl-ammonium chloride (S)-2-Benzyloxycarbonylamino-3-(4-benzyloxy-3-dimethylsulfamoyloxy-phenyl)-propionic acid methyl ester (615 mg) was dissolved in methanol (30 ml) containing benzyl chloride (180 mg) and 5% palladium-carbon (60 mg). The mixture was stirred overnight under an atmosphere of hydrogen gas. The catalyst was removed by filtration and washed with methanol. Evaporation of the filtrate gave a gum which was crystallised by trituration with ether. (S)-2-(3-Dimethylsulfamoyloxy-4-hydroxy-phenyl)-1-methoxycarbonyl-ethyl-ammonium chloride was obtained as an off-white solid, 320 mg; NMR (500 MHz, d6 DMSO) 2.89 (3H, s), 2.97 (1H, dd J 14, 8), 3.01-3.08 (4H, m), 3.67 (3H, s), 4.19 (1H, t J 7), 6.84-6.88 (3H, m), 8.54 (ca 3H, br exch D2O), 9.58 (1H, s, exch D2O); HPLC/MS retention time 2.68 min, m/z 283 (MH+).

EXAMPLE 4

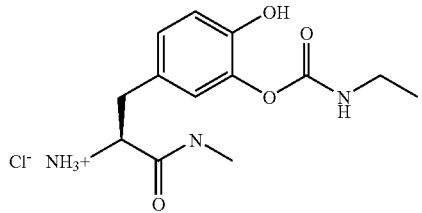

(S)-2-(3-Ethylcarbamoyloxy-4-hydroxy-phenyl)-1-methylcarbamoyl-ethyl-ammonium chloride Step 1

(S)-3-(4-Benzyloxy-3-hydroxy-phenyl)-2-tert-butoxycarbonylamino-propionic acid (S)-3-(4-Benzyloxy-3-ethylcarbamoyloxy-phenyl)-2-tert-butoxycarbonylamino-propionic acid methyl ester (example 1, step 2) (1.42 g) was dissolved in methanol (40 ml) and 2M lithium hydroxide (1.5 ml) was added. After 30 min a second portion of lithium hydroxide (1.6 ml) was added and the solution left for 2 days. Lithium hydroxide (2M, 0.2 ml) was added and the solution allowed to stand at room temperature for a further period of 7 days.

The solution was concentrated, diluted with water, acidified with dil. HCl and extracted with ethyl acetate. The extract was washed with water and with brine. Drying (MgSO4) and evaporation gave the crude product. Trituration with ether gave (S)-3-(4-benzyloxy-3-hydroxy-phenyl)-2-tert-butoxycarbonylamino-propionic acid as a white solid, 980 mg; NMR (500 MHz, d6 DMSO) 1.33 (9H, s), 2.67 (1H, dd J 13.5, 10), 2.84 (1H, dd J 13.3 4.5), 3.97-4.01 (1H, m), 5.05 (2H, s), 6.56 (1H, dd J 8, 2), 6.69 (1H, d J 2), 6.85 (1H, d J 8), 6.97 (1H, br d J 8), 7.29-7.46 (5H, m), 8.88 (1H, s exch D2O), 12.5 (1H br exch D2O); HPLC/MS retention time 5.37 min, m/z 388 (MH+).

Step 2

[(S)-2-(4-Benzyloxy-3-hydroxy-phenyl)-1-methylcarbamoyl-ethyl]-carbamic acid tert-butyl ester (S)-3-(4-benzyloxy-3-hydroxy-phenyl)-2-tert-butoxycarbonylamino-propionic acid (1.23 mmol) was dissolved in DMF (5 ml). EDCI (2 mmol) was added followed by HOBT (1 mmol) and methylamine hydrochloride (2 mmol). N,N-Diisopropylethylamine (2 mmol) was added and the solution was stirred at room temperature for 5 hours. The solution was diluted with water and ethyl acetate. The ethyl acetate extract was washed with dil HCl, with water and with brine. Drying (MgSO4) and evaporation gave the crude product which crystallised from ethyl acetate-hexane (1:1). [(S)-2-(4-Benzyloxy-3-hydroxy-phenyl)-1-methylcarbamoyl-ethyl]-carbamic acid tert-butyl ester was obtained as a white solid, 348 mg; HPLC/MS retention time 5.22 min, m/z 401 (MH+).

Step 3

[(S)-2-(4-Benzyloxy-3-ethylcarbamoyloxy-phenyl)-1-methylcarbamoyl-ethyl]-carbamic acid tert-butyl ester

[(S)-2-(4-Benzyloxy-3-hydroxy-phenyl)-1-methylcarbamoyl-ethyl]-carbamic acid tert-butyl ester (348 mg) was dissolved in dry dichloromethane (2 ml) and ethyl isocyanate (0.31 ml) added followed by a catalytic amount of DMAP. The solution was heated at 50° C. for 5 hours and a white solid formed. The mixture was diluted with ethyl acetate and the crude product was filtered off and washed with ethyl acetate. Recrystallisation from methanol afforded [(S)-2-(4-benzyloxy-3-ethylcarbamoyloxy-phenyl)-1-methylcarbamoyl-ethyl]-carbamic acid tert-butyl ester, 253 mg; HPLC/MS Retention time 5.49 min, m/z 472 (MH+).

Step 4

(S)-2-(3-Ethylcarbamoyloxy-4-hydroxy-phenyl)-1-methylcarbamoyl-ethyl-ammonium chloride

[(S)-2-(4-Benzyloxy-3-ethylcarbamoyloxy-phenyl)-1-methylcarbamoyl-ethyl]-carbamic acid tert-butyl ester (243 mg) was suspended in 4M HCl-dioxane (5 ml) and stirred at room temperature for 1 hour. The clear solution was evaporated to dryness giving an oil which was redissolved in methanol (5 ml). 5% Pd—C (50 mg) was added and the mixture stirred under an atmosphere of hydrogen gas at room temperature for 2 hours. The catalyst was removed by filtration and washed with methanol. Evaporation of the filtrate gave the crude product as an oil. Trituration with ether gave (S)-2-(3-ethylcarbamoyloxy-4-hydroxy-phenyl)-1-methylcarbamoyl-ethyl-ammonium chloride as a grey solid, 150 mg; NMR (500 MHz, d6 DMSO) 1.07 (3H, t J 7), 2.59 (3H, d J 4.5 collapse to s with D2O), 2.82-2.95 (2H, m), 3.03-3.10 (2H, m), 3.83 (1H, t J 7), 6.81-6.85 (3H, m), 7.55 (1H, t J 5.5), 8.19 (3H, br exch D2O), 8.37 (1H, br q exch D2O), 9.5 (1H, s, exch D2O); HPLC/MS Retention time 2.9 min, m/z 282 (MH+).

EXAMPLE 5

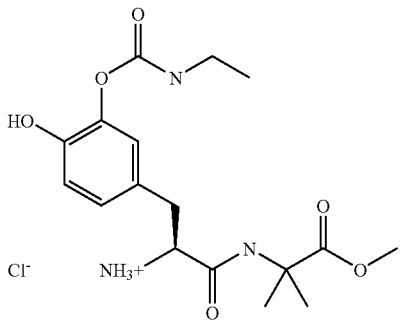

(S)-2-(3-Ethylcarbamoyloxy-4-hydroxy-phenyl)-1-(1-methoxycarbonyl-1-methyl-ethylcarbamoyl)-ethyl-ammonium chloride Step 1

2-[(S)-3-(4-Benzyloxy-3-hydroxy-phenyl)-2-tert-butoxycarbonylamino-propionylamino]-2-methyl-propionic acid methyl ester (S)-3-(4-benzyloxy-3-hydroxy-phenyl)-2-tert-butoxycarbonylamino-propionic acid (465 mg) was dissolved in anhydrous DMA (5 ml) and HBTU (910 mg) added in portions followed by methyl 2-aminoisobutyrate hydrochloride (366 mg). N,N-Diisopropylethylamine (0.4 ml) was added and the solution stirred at room temperature for 3 days. The mixture was diluted with water and ethyl acetate. The aqueous phase was extracted with ethyl acetate and the combined organic extracts were washed with dil HCl, with aq sodium bicarbonate with water and with brine. Drying (MgSO4) and evaporation of solvent gave the crude 2-[(S)-3-(4-benzyloxy-3-hydroxy-phenyl)-2-tert-butoxycarbonylamino-propionylamino]-2-methyl-propionic acid methyl ester as a gum, 690 mg; HPLC/MS retention time 5.77 min, m/z 487.

Step 2

2-[(S)-3-(4-Benzyloxy-3-ethylcarbamoyloxy-phenyl)-2-tert-butoxycarbony lamino-propionylamino]-2-methyl-propionic acid methyl ester 2-[(S)-3-(4-benzyloxy-3-hydroxy-phenyl)-2-tert-butoxycarbonylamino-propionylamino]-2-methyl-propionic acid methyl ester (1.2 mmol), was dissolved in dichloromethane (5 ml) and ethyl isocyanate (0.31 ml) added. A catalytic amount of DMAP was added and the solution was heated at 50° C. for 7 hours. The reaction mixture was evaporated to dryness and the crude product purified by chromatography on silica gel eluting with a mixture of ethyl acetate-hexane. 2-[(S)-3-(4-Benzyloxy-3-ethylcarbamoyloxy-phenyl)-2-tert-butoxycarbonylaminopropionyl-amino]-2-methyl-propionic acid methyl ester was obtained as a white crystalline solid, 410 mg; Rf 0.29 (ethyl acetate-hexane 1:1); NMR (500 MHz, CDCl3) 1.39 (ca 3H, s), 1.41 (ca 3H, s), 1.43 (ca 9H, s), 2.86 (1H, dd J 14, 8), 3.08 (1H, dd J 14, 5), 3.25-3.32 (2H, m), 3.70 (3H, s), 4.23 (1H, br), 5.00 (1H, br t J 5), 5.07 (2H, s), 6.15 (1H, s), 6.91 (1H, d J 8), 6.99-7.02 (2H, m), 7.28-7.42 (ca 5H, m); HPLC/MS retention time 5.98 min, m/z 558 (MH+).

Step 3

(S)-2-(3-Ethylcarbamoyloxy-4-hydroxy-phenyl)-1-(1-methoxycarbonyl-1-methyl-ethylcarbamoyl)-ethyl-ammonium chloride 2-[(S)-3-(4-Benzyloxy-3-ethylcarbamoyloxy-phenyl)-2-tert-butoxycarbony lamino-propionylamino]-2-methyl-propionic acid methyl ester (380 mg) was dissolved in 4M HCl-dioxane (10 ml) and stirred at room temperature for 1 hour. The solution was evaporated to dryness and the resulting gum was redissolved on methanol (10 ml) containing 5% Pd—C (60 mg). The mixture was stirred under an atmosphere of hydrogen for 2 hours. The catalyst was removed by filtration and the filtrate evaporated to dryness giving a gum. Repeated trituration with ether gave (S)-2-(3-ethylcarbamoyloxy-4-hydroxy-phenyl)-1-(1-methoxycarbonyl-1-methyl-ethylcarbamoyl)-ethyl-ammonium chloride as a white solid, 240 mg; NMR (500 MHz, d6 DMSO) 1.07 (ca 3H, t J 7), 1.32 (3H, s), 1.38 (3H, s), 2.85 (1H, dd J 14, 7), 2.98 (1H, dd J 14, 5), 3.05-3.09 (2H, m), 3.58 (3H, s), 3.91 (1H, br t), 6.83 (1H, d J 8), 6.91 (1H, dd J 8, 2), 6.94 (1H, d J 2), 7.55 (1H, br t), 8.15 (3H, br s exch D2O), 8.82 (1H, exch D2O), 9.51 (1H, s, exch D2O); HPLC/MS retention time 4.29 min, m/z 368 (MH+).

EXAMPLE 6

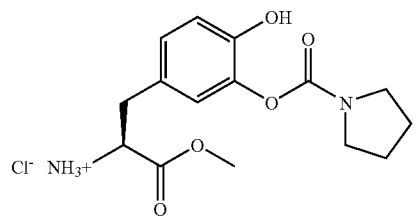

(S)-2-[4-Hydroxy-3-(pyrrolidine-1-carbonyloxy)-phenyl]-1-methoxycarbon yl-ethyl-ammonium chloride Step 1

Pyrrolidine-1-carboxylic acid 2-benzyloxy-5-((S)-2-benzyloxycarbonylamino-2-methoxycarbonyl-ethyl)-phenyl ester (S)-2-Benzyloxycarbonylamino-3-(4-benzyloxy-3-hydroxy-phenyl)-propionic acid methyl ester (434 mg) was dissolved in dichloromethane (7 ml) and a solution of 1-pyrrolidinylcarbonyl chloride (200 mg) in dichloromethane (2 ml) was added. Triethylamine (0.22 ml) was added dropwise followed by a catalytic amount of DMAP. The mixture was stirred and heated at 40° C. overnight. The reaction was monitored by HPLC/MS and further portions of 1-pyrrolidinylcarbonyl chloride (400 mg) and triethylamine (0.4 ml) were added and heating continued at 55 C for 48 hours. The reaction mixture was diluted with dichloromethane and washed with dil HCl, with aq sodium bicarbonate and with brine. Drying (MgSO4) and evaporation gave the crude product. Silca gel chromatography, eluting with mixtures of ethyl acetate-hexane gave pyrrolidine-1-carboxylic acid 2-benzyloxy-5-((S)-2-benzyloxycarbonylamino-2-methoxycarbonyl-ethyl)-phenyl ester as a colourless gum, 364 mg; Rf 0.3 (ethyl acetate-hexane 1:1); HPLC/MS retention time 7.31 min, m/z 533 (MH+).

Step 2

(S)-2-[4-Hydroxy-3-(pyrrolidine-1-carbonyloxy)-phenyl]-1-methoxycarbon yl-ethyl-ammonium chloride Pyrrolidine-1-carboxylic acid 2-benzyloxy-5-((S)-2-benzyloxycarbonylamino-2-methoxycarbonyl-ethyl)-phenyl ester (364 mg) was dissolved in methanol (15 ml) containing benzyl chloride (95 mg) and 5% palladium-carbon (50 mg). The mixture was stirred for 3 hours under an atmosphere of hydrogen gas. The catalyst was removed by filtration and washed with methanol. Evaporation of the filtrate gave a gum which was crystallised by trituration with ether. (S)-2-[4-Hydroxy-3-(pyrrolidine-1-carbonyloxy)-phenyl]-1-methoxycarbonyl-ethyl-ammonium chloride was obtained as a white solid, 212 mg; NMR (500 MHz, d6 DMSO) 1.82-1.92 (4H, m), 2.97 (1H, dd J 14, 7), 3.05 (1H, dd J 14, 6), 3.31 (2H, t J 7), 3.49 (2H, t J 7), 3.67 (3H, s), 4.19 (1H, t J ca 6), 6.85-6.88 (3H, m), 8.54 (3H, br s exch D2O), 9.54 (1H, s, exch D2O); HPLC/MS retention time 3.04 min, m/z 309 (MH+).

EXAMPLE 7

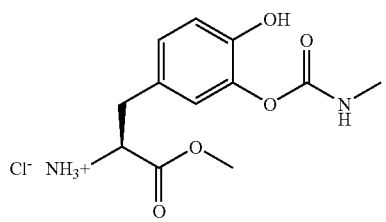

(S)-2-(4-Hydroxy-3-methylcarbamoyloxy-phenyl)-1-methoxycarbonyl-ethyl-ammonium chloride Step 1

(S)-2-Benzyloxycarbonylamino-3-(4-benzyloxy-3-methylcarbamoyloxy-phenyl)-propionic acid methyl ester A solution of (S)-2-Benzyloxycarbonylamino-3-(4-benzyloxy-3-hydroxy-phenyl)-propionic acid methyl ester (664 mg) and catalytic DMAP in dichloromethane (4 ml) was added to a flask containing methyl isocyanate (260 mg). The solution was stirred and heated at 40° C. overnight. The reaction was monitored by HPLC/MS and a further portion of methyl isocyanate (240 mg) was added and heating continued at 40° C. for 24 hours. The reaction mixture was evaporated to give the crude product which was purified by silica gel chromatography, eluting with mixtures of ethyl acetate-hexane. (S)-2-Benzyloxycarbonylamino-3-(4-benzyloxy-3-methylcarbamoyl-oxy-phenyl)-propionic acid methyl ester was obtained as a white solid, 437 mg; Rf 0.23 (ethyl acetate-hexane 1:1); HPLC/MS Retention time 6.55 min, m/z 493 (MH+).

Step 2

(S)-2-(4-Hydroxy-3-methylcarbamoyloxy-phenyl)-1-methoxycarbonyl-ethyl-ammonium chloride (S)-2-Benzyloxycarbonylamino-3-(4-benzyloxy-3-methylcarbamoyloxy-phenyl)-propionic acid methyl ester (427 mg) was dissolved in methanol (40 ml) containing 5% Pd—C (46 mg) and benzyl chloride (140 mg). The mixture was stirred under an atmosphere of hydrogen for 4 hours. The catalyst was removed by filtration and washed with methanol. The filtrate was evaporated to dryness giving a gum which was triturated with ether. (S)-2-(4-Hydroxy-3-methylcarbamoyloxy-phenyl)-1-methoxycarbonyl-ethyl-ammonium chloride was obtained as a white solid, 239 mg; NMR (500 MHz, d6 DMSO) 2.64 (ca 3H, d J 5), 2.97 (1H, dd J 14.5, 7), 3.04 (1H, dd J 14.5, 6), 3.67 (3H, s), 4.19 (1H, t J 6.5), 6.82-6.88 (3H, m), 7.44 (1H, q J 5 s exch D2O), 8.52 (3H, br s exch D2O), 9.57 (1H, s, exch D2O); HPLC/MS retention time 3.04 min, m/z 309 (MH+).

EXAMPLE 8

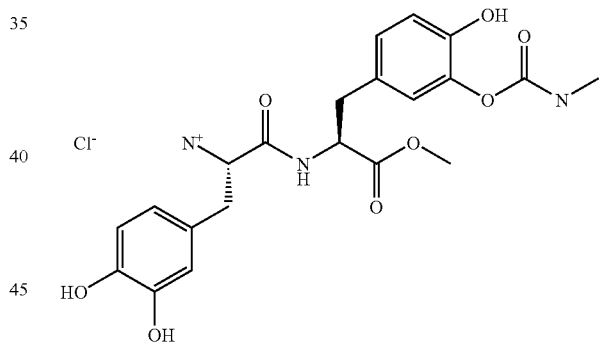

(S)-2-(3,4-Dihydroxy-phenyl)-1-[(S)-2-(4-hydroxy-3-methylcarbamoyloxy-phenyl)-1-methoxycarbonyl-ethylcarbamoyl]-ethyl-ammonium chloride Step 1

(S)-3-(4-Benzyloxy-3-methylcarbamoyloxy-phenyl)-2-tert-butoxycarbonylamino-propionic acid methyl ester N-Succinimidyl N-methylcarbamate (1.89 g, 11 mmol) was added to a solution of (S)-3-(4-Benzyloxy-3-hydroxyphenyl)-2-tert-butoxycarbonylamino-propionic acid methyl ester (1.1 g, 2.74 mmol) in acetonitrile (15 ml). The mixture was refluxed 4 days. After removal of the solvent, the residue was purified by silica gel chromatography eluting with ethyl acetate/hexane (2:3). (S)-3-(4-Benzyloxy-3-methylcarbamoyloxy-phenyl)-2-tert-butoxycarbonylamino-propionic acid methyl ester was obtained as a white solid, 0.83 g. 1H NMR (400 MHz, CDCl3) 1.42 (s, 9H), 2.86 (d, J=4.9 Hz, 3H), 3.01 (m, 2H), 3.70 (s, 3H), 4.53 (m, 1H), 5.00 (m, 2H), 5.07 (s, 2H), 6.89 (m, 3H), 7.29-7.42 (m, 5H).

Step 2

(S)-2-(4-Benzyloxy-3-methylcarbamoyloxy-phenyl)-1-methoxycarbonyl-ethyl-ammonium chloride To a solution of (S)-3-(4-Benzyloxy-3-methylcarbamoyloxy-phenyl)-2-tert-butoxy-carbonylamino-propionic acid methyl ester (0.80 g) in dichloromethane (10 ml) was added HCl solution (4M in dioxane, 4 ml) at 0° C. The mixture was stirred at this temperature for 2 h. Diethyl ether was added and a white solid precipitated. (S)-2-(4-Benzyloxy-3-methylcarbamoyloxy-phenyl)-1-methoxycarbonyl-ethyl-ammonium chloride was obtained by filtration as a white solid, 0.654 g. 1H NMR (400 MHz, d$_6$-DMSO) 2.65 (d, 3H), 3.01-3.14 (m, 2H), 3.67 (s, 3H), 4.24 (m, 1H), 5.10 (s, 2H), 7.01-7.11 (m, 3H), 7.30-7.44 (m, 5H), 7.61 (m, 1H), 8.64 (br, 3H).

Step 3

(S)-2-[(S)-2-Benzyloxycarbonylamino-3-(3,4-bis-benzyloxy-phenyl)-propionylamino]-3-(4-benzyloxy-3-methylcarbamoyloxy-phenyl)-propionic acid methyl ester (S)-2-(4-Benzyloxy-3-methylcarbamoyloxy-phenyl)-1-methoxycarbonyl-ethyl-ammonium chloride (0.2 g, 0.506 mmol) was suspended in dichloromethane (20 ml), then triethylamine (0.068 g, 0.678 mmol) was added, followed by the addition of (S)-2-benzyloxycarbonylamino-3-(3,4-bis-benzyloxy-phenyl)-propionic acid (0.31 g, 0.678 mmol) [see German patent DE 2121187] and HOBt (0.092 g, 0.678 mmol). The mixture was stirred at room temperature for 20 min. EDC (0.130 g, 0.678 mmol) was added. The stirring was continued overnight. The mixture was washed with sodium bicarbonate, dried over sodium sulfate. After removal of the solvent, the residue was purified by silica gel chromatography eluting with ethyl acetate/dichloromethane (1:2). (S)-2-[(S)-2-benzyloxycarbonylamino-3-(3,4-bis-benzyloxy-phenyl)-propionylamino]-3-(4-benzyloxy-3-methylcarbamoyloxy-phenyl)-propionic acid methyl ester was obtained as a white solid, 0.43 g. 1H NMR (400 MHz, CDCl3) 2.62 (d, J=4.6 Hz, 3H), 2.88-3.00 (m, 3H), 3.35 (s, 1H), 3.56 (s, 3H), 4.24-4.30 (m, 1H), 4.43-4.49 (m, 1H), 4.95 (m, 2H), 5.06 (m, 6H), 6.80 (m, 1H), 6.92-7.09 (m, 5H), 7.23-7.45 (m, 21H), 7.59 (m, 1H), 8.46 (d, J=7.3 Hz, 1H).

Step 4

(S)-1-[(S)-2-(4-Benzyloxy-3-methylcarbamoyloxy-phenyl)-1-methoxycarbonyl-ethylcarbamoyl]-2-(3,4-bis-benzyloxy-phenyl)-ethyl-ammonium; chloride (S)-2-[(S)-2-Benzyloxycarbonylamino-3-(3,4-bis-benzyloxy-phenyl)-propionylamino]-3-(4-benzyloxy-3-methylcarbamoyloxy-phenyl)-propionic acid methyl ester (0.95 g, 1.115 mmol) was suspended in ethyl acetate (20 ml) and methanol (20 ml). Pd/C (5%, 0.19 g) and benzyl chloride (0.155 g, 1.226 mmol) were added. The hydrogenation was carried out under 30 psi of hydrogen for 3 h. After filtration and removal of solvent, the residue was redissolved in methanol (3 ml) and diethyl ether was added and a white solid precipitated. (S)-1-[(S)-2-(4-Benzyloxy-3-methylcarbamoyloxy-phenyl)-1-methoxycarbonyl-ethylcarbamoyl]-2-(3,4-bis-benzyloxy-phenyl)-ethyl-ammonium chloride was obtained as white solid by filtration, 0.52 g. 1H NMR (400 MHz, d$_6$-DMSO) 2.63 (d, 3H), 2.73 (m, 1H), 2.82-3.01 (m, 3H), 3.61 (s, 3H), 3.92 (m, 1H), 4.46 (m, 1H), 6.52 (m, 1H), 6.68 (m, 2H), 6.83-6.91 (m, 3H), 7.50 (m, 1H), 8.11 (br, 3H), 8.87 (s, 1H), 8.97 (s, 1H), 9.10 (d, J=7.6 Hz, 1H), 9.57 (s, 1H). m/z 448 (MH+). HPLC/MS (Method B) retention time 4.58 min, m/z 448 (MH$^+$).

EXAMPLE 9

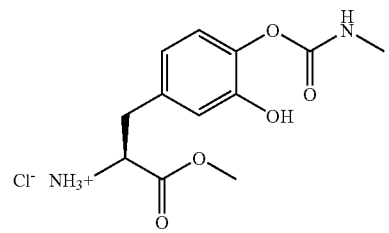

(S)-2-(3-Hydroxy-4-methylcarbamoyloxy-phenyl)-1-methoxycarbonyl-ethylammonium chloride Step 1

(S)-3-(3-Benzyloxy-4-methylcarbamoyloxy-phenyl)-2-tertbutoxycarbonylamino-propionic acid methyl ester A mixture of (S)-3-(3-benzyloxy-4-hydroxy-phenyl)-2-tert-butoxycarbonylamino-propionic acid methyl ester (1.15 g, 2.87 mmol) and N-succinimidyl N-methylcarbamate (1.975 g, 11.47 mmol) in acetonitrile (15 mL) was refluxed 4 days. After the removal of solvent, the residue was purified with chromatography using EtOAc/hexane (1:1.5) as an eluent to obtain (S)-3-(3-benzyloxy-4-methylcarbamoyloxy-phenyl)-2-tert-butoxycarbonylamino-propionic acid methyl ester as a white solid, 0.83 g. $^1$H NMR (400 MHz, CDCl3) 1.43 (s, 9H), 2.86 (d, 3H), 3.03 (m, 2H), 3.66 (s, 3H), 4.56 (m, 1H), 4.98 (m, 2H), 5.05 (s, 2H), 6.70-6.90 (m, 2H), 7.03 (m, 1H), 7.29-7.43 (m, 5H).

Step 2

(S)-2-(3-Benzyloxy-4-methylcarbamoyloxy-phenyl)-1-methoxycarbonyl-ethyl-ammonium chloride To a solution of (S)-3-(3-benzyloxy-4-methylcarbamoyloxy-phenyl)-2-tert-butoxycarbonylamino-propionic acid methyl ester (0.90 g) in dichloromethane (12 ml) cooled with an ice-bath was added 4 M HCl in dioxane (6 ml). The mixture was stirred at 0° C. for 2 h. Diethyl ether was added and a white solid was precipitated. (S)-2-(3-Benzyloxy-4-methylcarbamoyloxy-phenyl)-1-methoxycarbonyl-ethyl-ammonium chloride was obtained as white solid by filtration, 0.83 g. 1H NMR (400 MHz, d$_6$-DMSO) 2.64 (s, 3H), 3.10 (m, 2H), 3.68 (s, 3H), 4.33 (m, 1H), 5.10 (s, 2H), 6.79 (m, 1H), 7.04-7.12 (m, 2H), 7.32-7.45 (m, 5H), 7.60 (m, 1H), 8.64 (s, 3H).

Step 3

(S)-2-(3-Hydroxy-4-methylcarbamoyloxy-phenyl)-1-methoxycarbonyl-ethylammonium chloride (S)-2-(3-Benzyloxy-4-methylcarbamoyloxy-phenyl)-1-methoxycarbonyl-ethyl-ammonium chloride (0.5 g) was dissolved in methanol (30 mL), followed by the addition of 0.96 g Pd/C (5%). Hydrogenation was carried out under 30 psi of hydrogen at room temperature for 2 hours. After filtration, the filtrate was concentrated in vacuo and the residue was washed with diethyl ether. (S)-2-(3-Hydroxy-4-methylcarbamoyloxy-phenyl)-1-methoxycarbonyl-ethylammonium chloride was obtained as a white solid, 0.35 g. $^1$H NMR (400 MHz, $d_6$-DMSO) 2.63 (d, 3H), 2.96-3.09 (m, 2H), 3.70 (s, 3H), 4.22 (m, 1H), 6.61 (m, 1H), 6.74 (m, 1H), 6.91 (m, 1H), 7.46 (m, 1H), 8.60 (s, 3H), 9.65 (s, 1H). MS m/z (MH$^+$) 269. HPLC/MS (Method B) retention time 4.03 min, m/z 269 (MH$^+$).

EXAMPLE 10

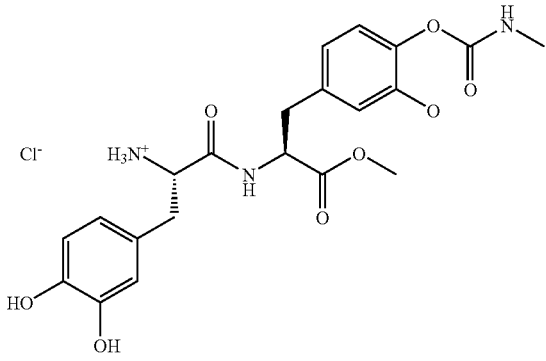

(S)-2-(3,4-Dihydroxy-phenyl)-1-[(S)-2-(3-hydroxy-4-methylcarbamoyloxy-phenyl)-1-methoxycarbonyl-ethylcarbamoyl]-ethyl-ammonium chloride Step 1

(S)-2-[(S)-2-Benzyloxycarbonylamino-3-(3,4-bis-benzyloxy-phenyl)-propionylamino]-3-(3-benzyloxy-4-methylcarbamoyloxy-phenyl)-propionic acid methyl ester (S)-2-(3-Benzyloxy-4-methylcarbamoyloxy-phenyl)-1-methoxycarbonyl-ethyl-ammonium chloride was suspended in dichloromethane (20 ml), then triethylamine (0.18 g) was added, followed by the addition of (S)-2-benzyloxycarbonylamino-3-(3,4-bis-benzyloxy-phenyl)-propionic acid (0.85 g), [see German patent DE 2121187], and HOBt (0.25 g). The mixture was stirred at room temperature for 20 min. EDC (0.35 g) was added and stirring was continued overnight. The mixture was washed with sodium bicarbonate, dried over sodium sulfate. After removal of the solvent, the residue was purified by silica gel chromatography eluting with ethyl acetate/dichloromethane (1:2). (S)-2-[(S)-2-Benzyloxycarbonylamino-3-(3,4-bis-benzyloxy-phenyl)-propionylamino]-3-(3-benzyloxy-4-methylcarbamoyloxy-phenyl)-propionic acid methyl ester was obtained as a white solid, 1.25 g. 1H NMR (400 MHz, CDCl3) 2.63 (d, J=4.6 Hz, 3H), 2.87-3.06 (m, 4H), 3.56 (s, 3H), 4.28-4.34 (m, 1H), 4.53-4.58 (m, 1H), 4.86-5.09 (m, 8H), 6.78 (m, 2H), 6.95 (m, 2H), 7.09 (m, 2H), 7.20-7.54 (m, 22H), 8.51 (m, 1H).

Step 2

(S)-2-(3,4-Dihydroxy-phenyl)-1-[(S)-2-(3-hydroxy-4-methylcarbamoyloxy-phenyl)-1-methoxycarbonyl-ethylcarbamoyl]-ethyl-ammonium chloride (S)-2-[(S)-2-Benzyloxycarbonylamino-3-(3,4-bis-benzyloxy-phenyl)-propionylamino]-3-(3-benzyloxy-4-methylcarbamoyloxy-phenyl)-propionic acid methyl ester (0.40 g, 0.470 mmol) was suspended in ethyl acetate (20 ml) and methanol (20 ml). Pd/C (5%, 0.10 g) and benzyl chloride (0.065 g, 0.517 mmol) were added. The hydrogenation was carried out under 30 psi of hydrogen for 3 h. After filtration and removal of solvent, the residue was redissolved in methanol (2 ml). Diethyl ether was added and a white solid precipitated. (S)-2-(3,4-Dihydroxy-phenyl)-1-[(S)-2-(3-hydroxy-4-methylcarbam-oyloxy-phenyl)-1-methoxycarbonyl-ethylcarbamoyl]-ethyl-ammonium chloride was obtained as a white solid by filtration, 0.22 g. 1H NMR (400 MHz, $d_6$-DMSO) 2.63 (d, 3H), 2.72 (m, 1H), 2.83-3.02 (m, 3H), 3.64 (s, 3H), 3.93 (m, 1H), 4.50 (m, 1H), 6.52 (m, 1H), 6.65 (m, 3H), 6.85 (m, 2H), 7.46 (m, 1H), 8.11 (s, 3H), 8.87 (s, 1H), 8.96 (s, 1H), 9.13 (m, 1H), 9.61 (s, 1H). m/z 448 (MH+).

EXAMPLE 11

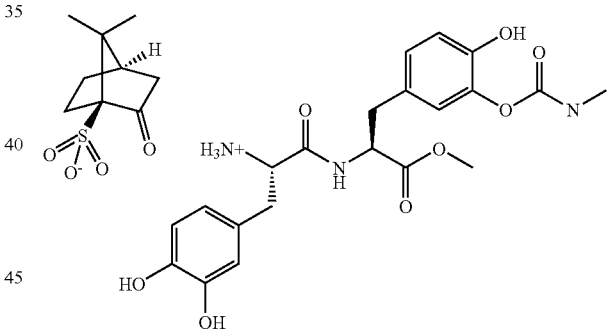

(S)-2-(3,4-Dihydroxy-phenyl)-1-[(S)-2-(4-hydroxy-3-methylcarbamoyloxy-phenyl)-1-methoxycarbonyl-ethylcarbamoyl]-ethyl-ammonium; (1S,4R)-2-Oxo-bicyclo[2.2.1]-heptane-1-sulfonate (S)-2-[(S)-2-Benzyloxycarbonylamino-3-(3,4-bis-benzyloxy-phenyl)-propionylamino]-3-(4-benzyloxy-3-methylcarbamoyloxy-phenyl)-propionic acid methyl ester (10.0 g, 11.7 mmol), 10% palladium on carbon (wet) (500 mg), (1R)-(−)-10-camphorsulfonic acid (2.76 g, 11.9 mmol) and dry methanol (100 mL) were charged to a 200 mL glass autoclave with magnetic stirrer bar. The vessel was purged with nitrogen then charged to 6 bar with hydrogen gas and the suspension was stirred rapidly at room temperature. After 1 h the pressure inside the vessel had reduced to 2 bar, the vessel was re-charged to 7 bar with hydrogen gas and stirring continued. After a total of 18 h the mixture was filtered through a glass microfibre filter paper (GF/F grade) and the filtrate quickly evaporated under reduced pressure (a 1 L evaporation flask was used, rotating at full speed with the water bath set at 45° C.). A solid foam had formed after 10 min, which was broken up and dried at 45° C. on the rotary evaporator for 2 h. (S)-2-(3,4-Dihydroxy-phenyl)-1-[(S)-2-(4-hydroxy-3-methylcarb-amoyloxy-phenyl)-1-methoxycarbonyl-ethylcarbamoyl]-ethyl-ammonium; (1S,4R)-2-Oxo-bicyclo[2.2.1]heptane-1-sulfonate was obtained as a free-flowing white solid (8.0 g). 1H NMR (400 MHz, $d_6$-DMSO) 0.75 (s, 3H), 1.03 (s, 3H), 1.27 (m, 2H), 1.86 (m, 1H), 1.94 (t, 1H), 2.24 (m, 1H), 2.64 (m, 3H), 2.69-2.76 (m, 2H), 2.73 (m, 1H), 2.81-2.97 (m, 3H), 3.64 (s, 3H), 3.86 (m, 1H), 4.49 (m, 1H), 6.49 (m, 1H), 6.67 (m, 2H), 6.79-6.83 (m, 3H), 7.45 (m, 1H), 7.77 (br, 3H), 8.85 (m, 1H), 8.87 (s, 1H), 8.79 (2, 1H), 9.38 (s, 1H). HPLC retention time 8.70 min

EXAMPLE 12

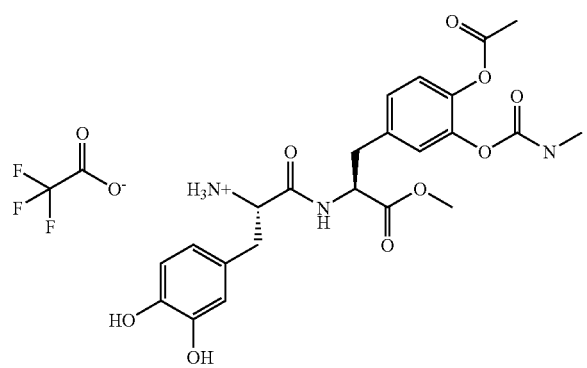

(S)-1-[(S)-2-(4-acetoxy-3-methylcarbamoyloxy-phenyl)-1-methoxycarbonyl-ethyl-carbamoyl]-2-(3,4-dihydroxy-phenyl)-ethyl-ammonium trifluoroacetate

Step 1

(S)-2-(4-Acetoxy-3-methylcarbamoyloxy-phenyl)-1-methoxycarbonyl-ethyl-ammonium chloride (S)-2-(4-Hydroxy-3-methylcarbamoyloxyphenyl)-1-methoxycarbonylethylammonium chloride (1.68 g, 6.26 mM) was dissolved in acetic acid (25 ml). HCl (g) was bubbled through the reaction mixture for 5 minutes before adding acetyl chloride (4.45 ml, 62.6 mM) dropwise. The reaction mixture was stirred at room temperature for 2 h. The mixture was concentrated to approximately half of its initial reaction volume. Diethyl ether was added to afford a solid. The solvent was evaporated and the residue was triturated with diethyl ether. The product was collected by filtration and dried under vacuum to constant weight to afford (S)-2-(4-Acetoxy-3-methylcarbamoyloxy-phenyl)-1-methoxycarbonyl-ethyl-ammonium chloride as a solid, 1.55 g. $^1$H-NMR (500 MHz, DMSO-$d_6$): δ=2.23 (s, 3H), 2.65 (d, J=4.6 Hz, 3H), 3.08-3.11 (m, J=14.35 Hz, 7.1 Hz, 1H), 3.14-3.17 (m, J=14.15 Hz, 5.9 Hz, 1H), 3.68 (s, 3H), 4.28 (t, 1H, CH), 7.10-7.17 (m, 3H), 7.70 (q, J=4.55 Hz, 1H), 8.59 (s, 3H). HPLC/MS (Method A) retention time 2.85 min, m/z 311 (MH+).

Step 2

(S)-3-(4-Acetoxy-3-methylcarbamoyloxyphenyl)-2-[(S)-2-benzyloxycarbonylamino-3-(3,4-bis-benzyloxyphenyl)-propionylamino]-propionic acid methyl ester (S)-2-(4-Acetoxy-3-methylcarbamoyloxy-phenyl)-1-methoxycarbonyl-ethyl-ammonium chloride (3.13 g, 9.03 mM), (S)-2-benzyloxycarbonylamino-3-(3,4-bis-benzyloxy-phenyl)-propionic acid (4.62 g, 9.03 mM) and EDCI (2.07 g, 10.83 mM) were dissolved in DMF (25 ml). Di-isopropylethylamine (2.43 g, 3.28 ml, 18.83 mM) was added and the reaction mixture stirred at room temperature for 4 h. Ethylacetate (200 ml) was added and the mixture was washed with water (3×250 ml). The organic layer was dried (MgSO$_4$), filtered and evaporated to dryness to afford a brown solid (6.93 g). The crude product was purified by column chromatography on silica gel eluting with CH$_2$Cl$_2$/EtOAc (gradient from 100% CH$_2$Cl$_2$ to CH$_2$Cl$_2$/ethyl acetate (from 0% ethyl acetate to 7:3) to afford (S)-3-(4-acetoxy-3-methylcarbamoyloxyphenyl)-2-[(S)-2-benzyloxycarbonylamino-3-(3,4-bis-benzyloxyphenyl)-propionylamino]-propionic acid methyl ester as a white solid, 4.57 g. $^1$H-NMR (500 MHz, CDCl$_3$): δ=2.23 (s, 3H), 2.69 ($s_{br}$, 3H), 2.87 ($s_{br}$, 1H), 2.95 (dd, J=13.95 Hz, 6.50 Hz, 1H), 3.02 (dd, J=14.1 Hz, 5.70 Hz, 1H), 3.11 (dd, J=13.9 Hz, 5.50 Hz, 1H), 3.33 (s, 3H), 4.43-4.44 (m, 1H), 4.84-4.85 (m, 1H), 5.00-5.08 (m, 6H,), 5.79 (d, J=7.25 Hz, 1H), 6.49 (d, J=6.85 Hz, 1H), 6.73 (dd, J=8.25 Hz, 1.75 Hz, 1H), 6.80-6.82 (m, J=8.2, 4H), 6.98-7.00 (m, 1H), 7.27-7.35 (m, 12H), 7.41-7.42 (m, 4H). HPLC/MS (Method A) retention time 7.14 min, m/z 805 (MH+).

Step 3

(S)-1-[(S)-2-(4-acetoxy-3-methylcarbamoyloxyphenyl)-1-methoxycarbonylethyl-carbamoyl]-2-(3,4-dihydroxyphenyl)ethylammonium trifluoroacetate A round bottom flask was charged with (S)-3-(4-acetoxy-3-methylcarbam-oyloxyphenyl)-2-[(S)-2-benzyloxycarbonylamino-3-(3,4-bis-benzyloxyphenyl)-propion-ylamino]-propionic acid methyl ester (1.00 g, 1.24 mM) and dioxane/methanol [3:1] (40 ml) to afford a cloudy solution. The mixture was purged with nitrogen and 10% Pd/C (250 mg) was added portionwise followed by TFA (213 mg, 0.147 ml, 1.86 mM). The flask was purged with hydrogen and sealed with a hydrogen balloon. The reaction was stirred at room temperature and monitored by LCMS. After 3 h the catalyst was removed by filtration and washed with methanol (2×10 mL). The combined filtrates were concentrated in vacuo (water bath temperature 30° C.) to afford a colourless oil. The oil was triturated with diethyl ether to give a white solid. The supernatant was decanted and trituration was repeated with diethyl ether. The resulting white solid was dried under vacuum at 30° C. to constant weight to afford (S)-1-[(S)-2-(4-acetoxy-3-methylcarbamoyloxyphenyl)-1-methoxycarbonylethylcarbam-oyl]-2-(3,4-dihydroxyphenyl)ethylammonium trifluoroacetate as a white free-flowing powder, 719 mg. $^1$H-NMR (500 MHz, DMSO-$d_6$): δ=2.22 (s, 3H), 2.65 (d, J=4.6 Hz, 3H), 2.67-2.73 (m, 1H), 2.94-2.98 (m, 2H), 3.08 (dd, J=14.15 Hz, 5.55 Hz, 1H), 3.64 (s, 3H), 3.90 ($s_{br}$, 1H), 4.55-4.58 (m, 1H), 6.51 (dd, J=8.05 Hz, 1.95 Hz, 1H), 6.66-6.68 (m, 2H), 7.09 (dd, J=8.25 Hz, 1.95 Hz, 1H), 7.11-7.15 (m, 2H), 7.71 (q, J=4.55 Hz, 1H), 7.99 (br, 3H), 8.81 ($s_{br}$, 1H), 8.90 (s$_{br}$, 1H), 8.97 (d, J=7.65, 1H). HPLC/MS (Method A) retention time 3.20 min, m/z 490 (MH+).

EXAMPLE 13

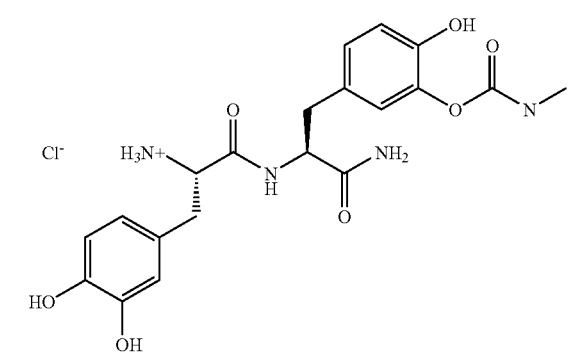

(S)-1-[(S)-1-Carbamoyl-2-(4-hydroxy-3-methylcarbamoyloxyphenyl)-ethylcarbamoyl]-2-(3,4-dihydroxyphenyl)-ethylammonium; chloride

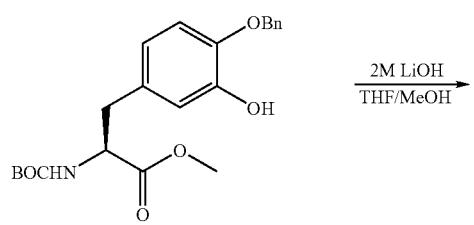

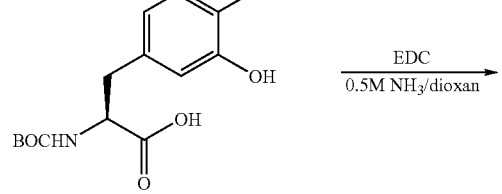

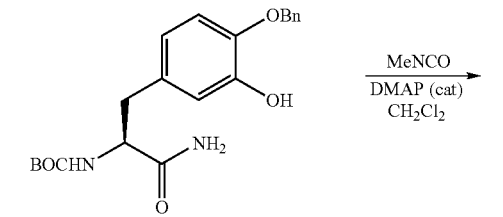

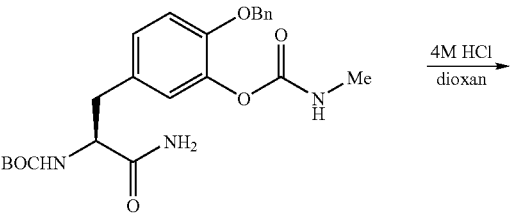

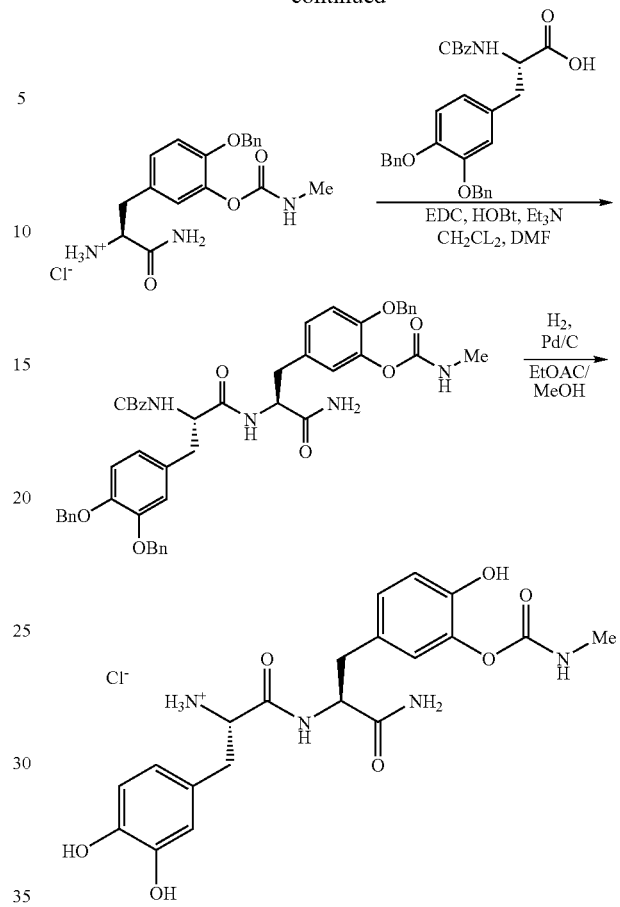

(S)-1-[(S)-1-Carbamoyl-2-(4-hydroxy-3-methylcarbamoyloxyphenyl)-ethylcarbamoyl]-2-(3,4-dihydroxyphenyl)-ethylammonium; chloride was prepared according to the route shown in scheme 1 to afford the product as a colourless solid 0.111 g. $^1$H-NMR (500 MHz, DMSO-d$_6$): δ=2.64 (d, J=4.6 Hz, 3H), 2.63-2.76 (m, 1H), 2.89-3.07 (m, 3H), 3.87 (m, 1H), 4.38-4.43 (m, 1H), 6.51-6-94 (m, 6H), 7.14 (m, 1H), 7.43-7.56 (m, 2H), 7.98 (b, 3H), 8.73-8.92 (m, 3H), 9.45 (s, 1H). MS m/z 433 (MH+).

Biological Results

A. Pharmacokinetic Analysis

Pharmacokinetics Dosing Protocol

Naïve male Wistar rats (bodyweight=250-500 g) were used for the pharmacokinetic studies. Animals were fasted overnight. The compound of interest was dissolved in 0.9% saline and co-dosed with Benserazide (10 mg/kg) at a molecular weight equivalent dose to 12.5 mg/kg L-Dopa. Blood samples were taken via a butterfly needle located into the lateral tail vein and collected into sample tubes containing heparin as the anti-coagulant. Blood samples were centrifuged at 5000 rpm for 10 minutes; the supernatant plasma was removed and stored at −80° C.

Preparation of Sample and Standard Solutions

Stock solutions of 10 mM L-Dopa and Warfarin were prepared in 20% TFA, 10 mM sodium meta bisulphite and DMSO, respectively.

Standard curves and Quality control (QC) samples were prepared by spiking control rat plasma with L-Dopa to achieve an initial concentration of 50 μM. Serial dilutions of this solution were performed in rat plasma to result in solutions with 25, 6.25, 3.125, 1.56, 0.78 and 0.39 μM L-Dopa.

One volume of sample plasma, standard and QC sample plasma was transferred from each sample vial to a 96 well plate. Compounds were extracted from plasma by addition of one volume of 20% TFA in 10 mM sodium meta bisulphite containing the internal standard, Warfarin, at 0.5 µM. The samples were vortex mixed and centrifuged at 4500 rpm for 4 minutes to precipitate plasma proteins. One volume of water was added to each well and the protein pellet was re-suspended. The samples were again vortex mixed and centrifuged at 4500 rpm for 9 minutes to precipitate plasma proteins.

The supernatant was analysed as detailed below.

LC-MS/MS Analysis

The LC-MS/MS system consisted of an Agilent 1100 series gradient HPLC pump (Agilent Technologies, Palo Alto, Calif.), a CTC HTS PAL Autosampler (CTC Analytics, Zwingen, Switzerland) and an Applied Biosystems/MDS Sciex API 3000 triple quadrupole mass spectrometer (Applied Biosystems, Foster City, Calif.) equipped with a turbo ionspray interface and operated in positive electrospray mode. Analytes in incubation mixtures were separated by reverse phase HPLC using a Phenomenex Sphereclone ODS 2 column (150×4.6 mm, 3 µm, Phenomenex, Torrance, Calif.).

A gradient elution program was used at a flow rate of 1 ml/min with a mobile phase consisting of acetonitrile/0.1% formic acid (5% v/v) in water/0.1% formic acid, delivered for 1.5 minutes, after which time the acetonitrile concentration was increased to 95% over 0.5 minutes and held at 95% for four minutes before restoring it back to 5% for the remaining two minutes. The injection volume was 20 µl. Approximately 10% of the eluent was introduced into the mass spectrometer source. The source temperature of the mass spectrometer was maintained at 450° C., and other source parameters (e.g., collision energy, declustering potential, curtain gas pressure etc.) were optimised on the day of analysis to achieve maximum sensitivity. Quantification of L-Dopa and Warfarin was achieved by monitoring the transitions of m/z=198.075/152.1 and m/z=369.069/163, respectively.

Non-compartmental analysis was performed using WinNonlin software (v 5.2 Professional version, Pharsight corporation, Mountain View, Calif.) on individual animal profiles to determine the area under the curve (AUC). Values were recorded as mean values+/−standard deviation.

In the above assay, all the Example compounds of the invention were shown to be converted in vivo to L-Dopa to varying extents and over varying periods of time.

B. Assessment of Activity in 6-OHDA-Lesioned Rats

Animals Male Wistar rats, 200-225 g on arrival, Harlan Ltd.

Housing Animals were housed in groups of 4 on a 12-h light-dark cycle with an environment of 50% humidity and temperature of 21±2° C. in accordance with Animals (Scientific Procedures) Act 1996 Home Office regulations. Rats had access to food and water ad libitum.

Licence All animals used in this study were treated in accordance with the UK 1986 Animals (Scientific Procedures) Act).

Procedure

Surgery Male Wistar rats were anaesthetized in an induction chamber using isofluorane (1-2% in 95% $O_2$, 5% $CO_2$ carrier gas), placed in a Kopf stereotaxic frame and anaesthesia maintained with 0.5-1.0% isofluorane. An incision was made in the scalp and a 0.8-mm-diameter hole made in the skull at coordinates AP: −2.6 mm, L: +2.0 mm (all co-ordinated measured from bregma). The neurotoxin 6-hydroxydopamine (6-OHDA) (8 µg free base in 4 µL of 0.9% saline containing 0.05% ascorbic acid) was injected into the left median forebrain bundle at a constant rate over 4 min (1 µl/min) using a 10-µL Hamilton syringe lowered to −8 mm below the dura. The needle remained in place for a further 4 min before being removed, and the wound cleaned and sutured. Carprofen (5 mg/kg subcutaneously) was administered for pain relief and a rehydration treatment of 5% glucose in 0.9% saline (up to 5 ml ip) was given prior to recovery from the anaesthetic.

Behavioural Assessment

Confirmation of the Lesion

At least 2 weeks following surgery, animals were examined for rotational behaviour (see below) in response to the administration of apomorphine hydrochloride (0.5 mg/kg s.c. in 0.9% saline containing 0.05% ascorbic acid) to evaluate the extent of the lesion. Only those rats exhibiting >6 turns/min at peak activity were used in future studies.

Assessment of the Induction of Rotational Activity by Test Compounds

At least 1 week after apomorphine administration, rats (n=4-8 per treatment) were tested for rotational activity with either a test drug or L-DOPA. These were administered either via the intraperitoneal (ip) route or orally by gavage (po). Animals were placed in rotometers (Med Associates) for up to 30 min to measure basal activity. They were then treated with benserazide (10 mg/kg) concomitantly with test compound or L-DOPA (63.4 µmole/kg ip or po). Rotation behaviour was assessed for up to 6 hours after test drug/L-DOPA administration. Animals were typically treated with a series of compounds for comparative purposes. Each treatment was administered at least 1 day apart.

Data Analysis

The number of rotations measured per 10 minutes over the 6 hour period was determined. Animals were considered active if they turned >10 turns per 10 minutes. From this data the following parameters were measured:

A Total activity (AUC activity, where AUC=area under the locomotor-activity/time curve)

B Peak activity

C Duration of activity

Values are quoted as % of L-DOPA induced effects.

By way of example, the compound of Example 8 above, administered p.o., demonstrated increased locomotor activity compared to baseline, with an AUC (locomotor activity) of 928 (±161) rotations per 220 min, peak locomotor activity at 92 (±20) rotations per 10 min and a duration of locomotor activity of 142 (±7) min.

The invention claimed is:

1. A compound which is a substituted phenylalanine of formula (I) or formula (II), or a salt or hydrate thereof:

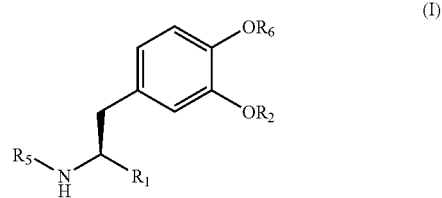

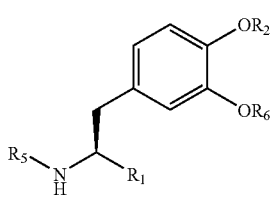

wherein:
R$_1$ is a carboxyl, carboxyl ester, or carboxamide group;
R$_2$ is a group —C(=O)—NR$_3$R$_4$, or —S(=O)$_2$—NR$_3$R$_4$;
R$_3$ and R$_4$ are independently selected from hydrogen, optionally substituted C$_1$-C$_6$ alkyl, (C$_1$-C$_5$ fluoroalkyl)-CH$_2$—, -Q, and —CH$_2$Q, wherein Q is an optionally substituted monocyclic carbocyclic or heterocyclic ring of 3 to 6 ring atoms; or R$_3$ and R$_4$ together with the nitrogen to which they are attached form an optionally substituted monocyclic cycloalkyl or non-aromatic heterocyclic ring of 3 to 8 ring atoms;
R$_5$ is hydrogen, or a natural or non-natural alpha amino acid residue linked via a peptide bond;
R$_6$ is hydrogen or a group R$_7$C(=O)—; and
R$_7$ is C$_1$-C$_6$ alkyl, C$_1$-C$_6$ fluoroalkyl or cyclopropyl.

2. A compound as claimed in claim 1 wherein R$_6$ is hydrogen.

3. A compound as claimed in claim 1 wherein R$_6$ is CH$_3$C(=O)—.

4. A compound as claimed in claim 1 wherein R$_2$ is a group —C(=O)—NR$_3$R$_4$.

5. A compound as claimed in claim 1 wherein one of R$_3$ and R$_4$ is hydrogen, and the other is C$_1$-C$_3$ alkyl.

6. A compound as claimed in claim 1 wherein R$_3$ is hydrogen and R$_4$ is methyl.

7. A compound as claimed in claim 1 wherein R$_3$ and R$_4$ together with the nitrogen to which they are attached form an optionally substituted piperidinyl, piperazinyl, morpholinyl or pyrrolidinyl ring.

8. A compound as claimed in claim 1 wherein any optional substituents are selected from trifluoromethyl, methoxy, trifluoromethoxy, halogen, cyano, hydroxy, mercapto, oxo, —NH$_2$, —NHR$^A$, and —NR$^A$R$^B$ wherein R$^A$ and R$^B$ are independently methyl or ethyl.

9. A compound as claimed in claim 1 wherein R$_1$ is a carboxyl group.

10. A compound as claimed in claim 1 wherein R$_1$ is a carboxyl ester group of formula —COOR$^C$ wherein R$^C$ is C$_1$-C$_6$ alkyl.

11. A compound as claimed in claim 10 wherein R$^C$ is methyl.

12. A compound as claimed in claim 1 wherein R$_1$ is —CONH$_2$.

13. A compound as claimed in claim 1 wherein R$_5$ is hydrogen.

14. A compound as claimed in claim 1 wherein R$_5$ is an alpha amino acid residue of formula —C(=O)C(R$_8$)(R$_9$)NH$_2$, wherein R$_8$ and R$_9$ are independently
(a) hydrogen; or
(b) the side chain of a natural amino acid, or
(c) optionally substituted C$_1$-C$_4$ alkyl, C$_1$-C$_4$ alkoxy, C$_2$-C$_4$ alkenyl, C$_2$-C$_4$ alkenyloxy, or C$_2$-C$_4$ alkynyl, or
(d) —CH$_2$XCH$_3$, —CH$_2$CH$_2$XCH$_3$, or —CH$_2$XCH$_2$CH$_3$, wherein X is —O—, S, or —NR$_{10}$ wherein R$_{10}$ is hydrogen, methyl or ethyl; or
(e) —CH$_2$Q or CH$_2$OQ wherein Q is as defined in claim 1; or R$_8$ and R$_9$ taken together with the carbon atom to which they are attached form an optionally substituted cycloalkyl or heterocyclic ring of 3 to 8 ring atoms, optionally fused to a second, optionally substituted, carbocyclic or heterocyclic ring.

15. A compound as claimed in claim 14 wherein one of R$_8$ and R$_9$ is hydrogen and the other is the side chain of a natural amino acid other than glycine.

16. A compound as claimed in claim 14 wherein R$_8$ and R$_9$ are independently optionally substituted C$_1$-C$_4$ alkyl, phenyl, benzyl cyclopropyl, cyclobutyl, cyclopentyl, cyclohexyl, cyclopropylmethyl, cyclobutylmethyl, cyclopentylmethyl, cyclohexylmethyl, pyridyl, pyridylmethyl, piperidinyl, piperazinyl or morpholinyl.

17. A compound as claimed in claim 15 wherein one of R$_8$ and R$_9$ is methyl.

18. A compound as claimed in claim 14 wherein R$_8$ and R$_9$ are each methyl.

19. A compound as claimed in claim 14 wherein R$_8$ and R$_9$ taken together with the carbon atom to which they are attached form a C$_1$-C$_6$ cycloalkyl ring, which is optionally benz-fused.

20. A compound as claimed in claim 14 wherein R$_8$ and R$_9$ taken together with the carbon atom to which they are attached form a cyclopropyl, cyclobutyl, cyclopentyl or cyclohexyl ring.

21. A compound as claimed in claim 14 wherein any optional substituents are selected from methyl, trifluoromethyl, methoxy, trifluoromethoxy, cyclopropyl, halogen, cyano, hydroxy, mercapto, oxo, —NH$_2$, —NHR$^A$, or —NR$^A$R$^B$ wherein R$^A$ and R$_B$ are independently methyl or ethyl.

22. A compound as claimed in claim 1 wherein R$_5$ is a group of formula (III):

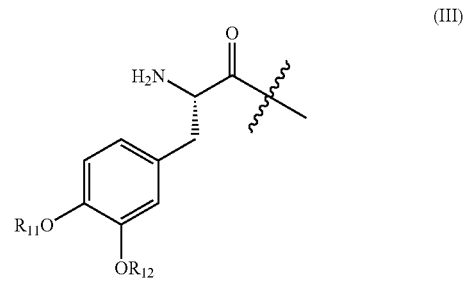

wherein (a) R$_{11}$ and R$_{12}$ are independently selected from hydrogen, groups R$_6$ as defined in claim 1, groups —C(=O)OR$_{13}$ or groups —C(=O)OR$_{13}$ wherein R$_{13}$ is C$_1$-C$_3$ alkyl; or (b) one of R$_{11}$ and R$_{12}$ is hydrogen and the other is a group R$_2$ as defined in claim 1.

23. A compound as claimed in claim 22 wherein R$_{11}$ and R$_{12}$ are each hydrogen.

24. A compound of formula (IV) or formula (V), or a salt or hydrate thereof:

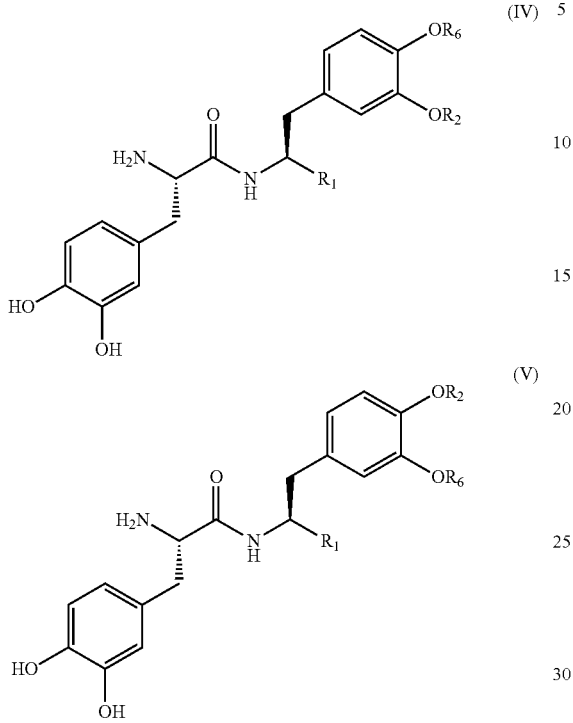

wherein $R_1$ is a group $R_{14}O(C=O)-$; $R_2$ is a group $R_{15}NH(C=O)-$; and $R_6$ is hydrogen or a group $R_{16}(C=O)-$, wherein $R_{14}$, $R_{15}$, and $R_{16}$ are independently selected from $C_1$-$C_6$ alkyl, $C_1$-$C_6$ fluoroalkyl and cyclopropyl.

25. A compound as claimed in claim 24 wherein $R_{14}$, $R_{15}$, and $R_{16}$ are each methyl.

26. A compound as claimed in claim 1 selected from the group consisting of:
  (S)-2-(3-Ethylcarbamoyloxy-4-hydroxy-phenyl)-1-methoxycarbonyl-ethyl-ammonium chloride;
  (S)-2-(3-Dimethylcarbamoyloxy-4-hydroxy-phenyl)-1-methoxycarbonyl-ethyl-ammonium chloride;
  (S)-2-(3-Dimethylsulfamoyloxy-4-hydroxy-phenyl)-1-methoxycarbonyl-ethyl-ammonium chloride;
  (S)-2-(3-Ethylcarbamoyloxy-4-hydroxy-phenyl)-1-methylcarbamoyl-ethyl-ammonium chloride;
  (S)-2-(3-Ethylcarbamoyloxy-4-hydroxy-phenyl)-1-(1-methoxycarbonyl-1-methyl-ethylcarbamoyl)-ethyl-ammonium chloride;
  (S)-2-[4-Hydroxy-3-(pyrrolidine-1-carbonyloxy)-phenyl]-1-methoxycarbonyl-ethyl-ammonium chloride;
  (S)-2-(4-Hydroxy-3-methylcarbamoyloxy-phenyl)-1-methoxycarbonyl-ethyl-ammonium chloride;
  (S)-2-(3,4-Dihydroxy-phenyl)-1-[(S)-2-(4-hydroxy-3-methylcarbamoyloxy-phenyl)-1-methoxycarbonyl-ethylcarbamoyl]-ethyl-ammonium chloride;
  (S)-2-(3-Hydroxy-4-methylcarbamoyloxy-phenyl)-1-methoxycarbonyl-ethylammonium chloride;
  (S)-2-(3,4-Dihydroxy-phenyl)-1-[(S)-2-(3-hydroxy-4-methylcarbamoyloxy-phenyl)-1-methoxycarbonyl-ethylcarbamoyl]-ethyl-ammonium chloride;
  (S)-2-(3,4-Dihydroxy-phenyl)-1-[(S)-2-(4-hydroxy-3-methylcarbamoyloxy-phenyl)-1-methoxycarbonyl-ethylcarbamoyl]-ethyl-ammonium; (1S,4R)-2-oxo-bicyclo[2.2.1]heptane-1-sulfonate;
  (S)-1-[(S)-2-(4-acetoxy-3-methylcarbamoyloxy-phenyl)-1-methoxycarbonyl-ethylcarbamoyl]-2-(3,4-dihydroxy-phenyl)-ethyl-ammonium trifluoroacetate; and
  (S)-1-[(S)-1-Carbamoyl-2-(4-hydroxy-3-methylcarbamoyloxyphenyl)-ethylcarbamoyl]-2-(3,4-dihydroxyphenyl)-ethylammonium; chloride,
or a salt or hydrate thereof.

27. A pharmaceutical composition comprising a compound as claimed in claim 1 together with a pharmaceutically acceptable carrier.

28. The composition as claimed in claim 27 wherein the compound is present in an amount effective for treatment of a condition associated with impaired dopaminergic signalling.

29. A method of treatment of a condition associated with impaired dopaminergic signalling in a subject, comprising administrating to the subject an amount of a compound as claimed in claim 1 effective to reduce such impairment of dopaminergic signalling.

30. The method as claimed in claim 29, wherein the condition is Parkinson's disease, or Restless Legs Syndrome.

31. The method as claimed in claim 29, wherein the condition is Tourette's syndrome, attention deficit hyperactive disorder, generation of pituitary tumours, a Parkinson-plus syndrome, levodopa responsive dystonia, dyskinesia, periodic movements in sleep, dysphagia or neuroleptic malignant syndrome.

\* \* \* \* \*